(12) United States Patent
Sharma et al.

(10) Patent No.: US 12,239,291 B2
(45) Date of Patent: Mar. 4, 2025

(54) MEDICAL SYSTEMS, DEVICE, AND RELATED METHODS THEREOF

(71) Applicants: Boston Scientific Scimed, Inc., Maple Grove, MN (US); Boston Scientific Medical Device Limited, Galway (IE)

(72) Inventors: Deepak Kumar Sharma, Muzaffarnagar (IN); James J. Scutti, Norwell, MA (US)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 319 days.

(21) Appl. No.: 17/808,011

(22) Filed: Jun. 21, 2022

(65) Prior Publication Data

US 2022/0400932 A1    Dec. 22, 2022

Related U.S. Application Data

(60) Provisional application No. 63/213,632, filed on Jun. 22, 2021.

(51) Int. Cl.
| | | |
|---|---|---|
| *A61B 1/005* | (2006.01) | |
| *A61B 1/00* | (2006.01) | |
| *A61B 1/008* | (2006.01) | |

(52) U.S. Cl.
CPC ........ *A61B 1/0052* (2013.01); *A61B 1/00105* (2013.01); *A61B 1/00112* (2013.01); *A61B 1/008* (2013.01)

(58) Field of Classification Search
CPC .............. A61B 1/0052; A61B 1/00105; A61B 1/00112; A61B 1/008; A61B 2017/00323; A61B 2017/00424; A61B 10/06; A61B 2017/003; A61B 2017/00438; A61B 2017/291; A61B 17/2909; A61B 17/00234
See application file for complete search history.

(56) References Cited

U.S. PATENT DOCUMENTS

| | | |
|---|---|---|
| 2004/0181138 A1 | 9/2004 | Hindricks et al. |
| 2005/0096694 A1 | 5/2005 | Lee |
| 2009/0054734 A1 | 2/2009 | DeSantis et al. |
| 2013/0237907 A1 | 9/2013 | Bacher et al. |
| 2019/0350643 A1 | 11/2019 | Osada et al. |
| 2020/0170701 A1 | 6/2020 | O'Keefe et al. |

FOREIGN PATENT DOCUMENTS

WO    2020110282 A1    6/2020

OTHER PUBLICATIONS

International Search Report and Written Opinion in International Application No. PCT/US2022/073046, mailed Oct. 7, 2022 (13 pages).

*Primary Examiner* — Richard G Louis
(74) *Attorney, Agent, or Firm* — Bookoff McAndrews PLLC

(57) ABSTRACT

A medical device comprising a handle extending between a first end and a second end, a first actuator coupled to the first end of the handle, a first shaft coupled to the second end of the handle, and a second shaft extending from the first shaft, the second shaft including a first articulation section and a second articulation section, wherein an articulation of the first actuator relative to the handle is configured to articulate the first articulation section, an articulation of the handle relative to the first shaft is configured to articulate the second articulation section, and the first articulation section and the second articulation section are restricted to articulating only in a first plane.

20 Claims, 16 Drawing Sheets

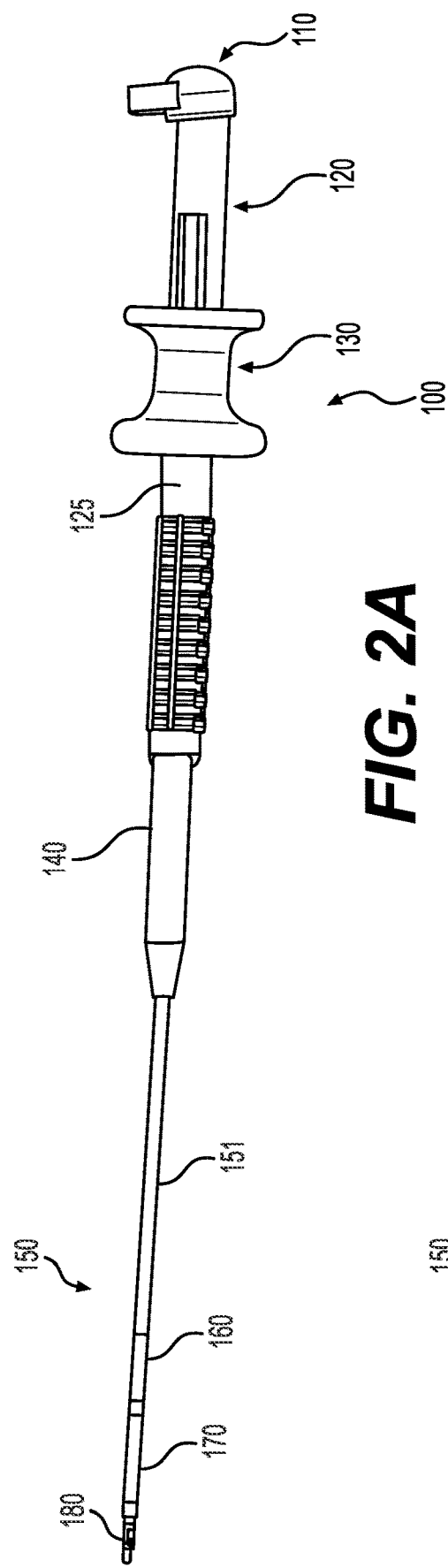
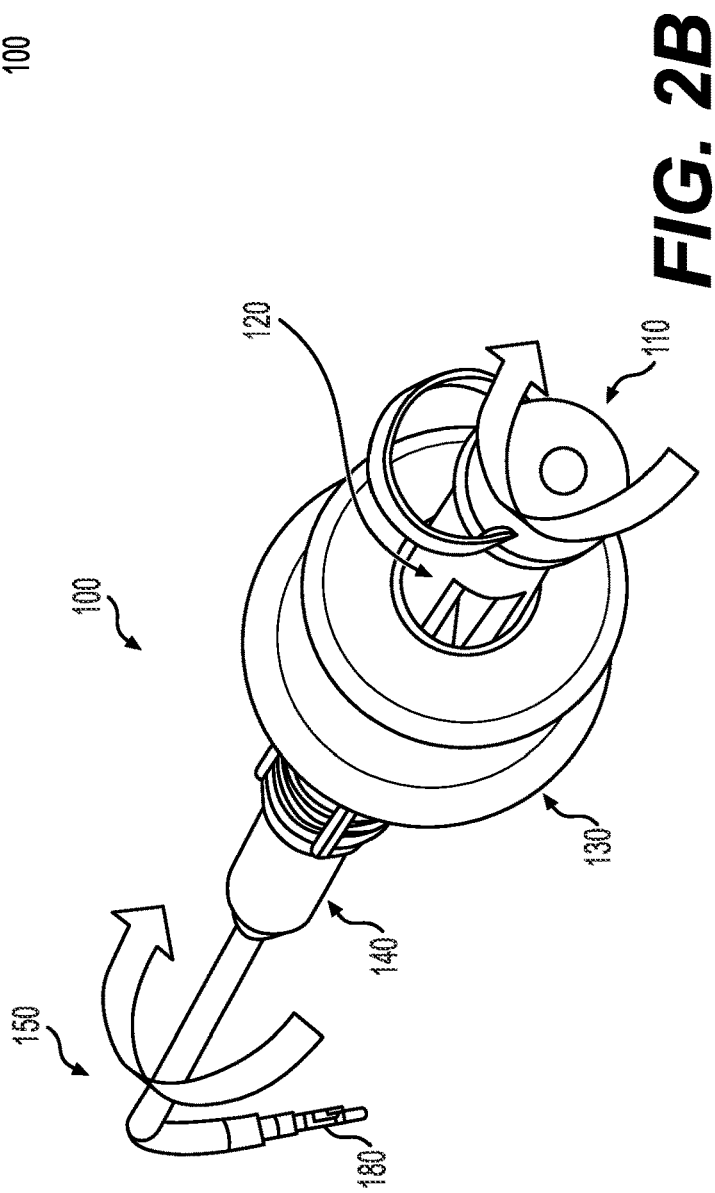
FIG. 2A
FIG. 2B

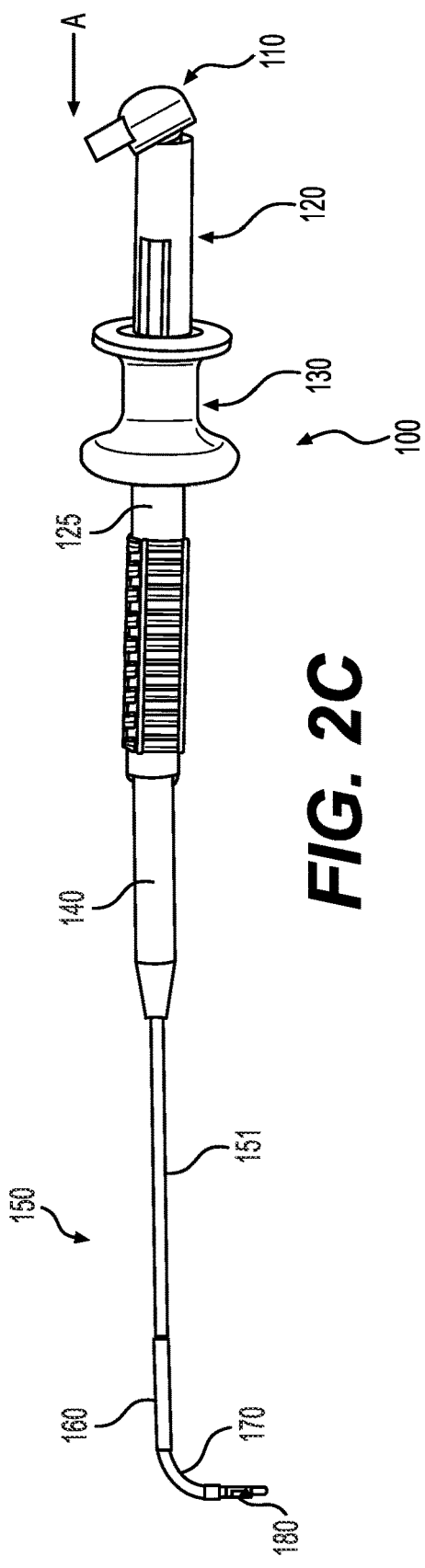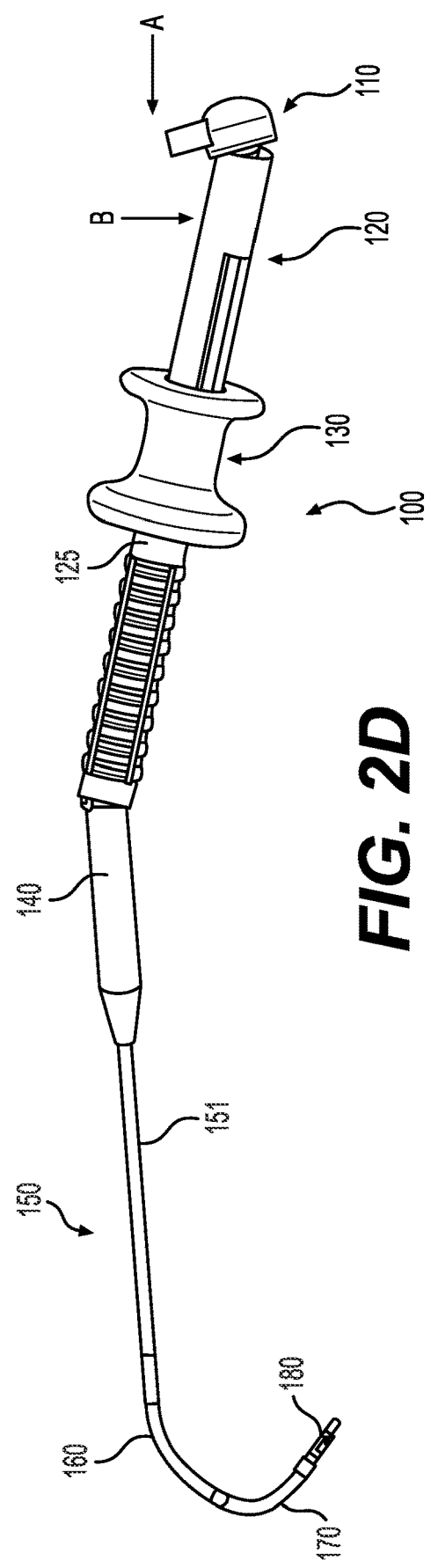
FIG. 2C
FIG. 2D

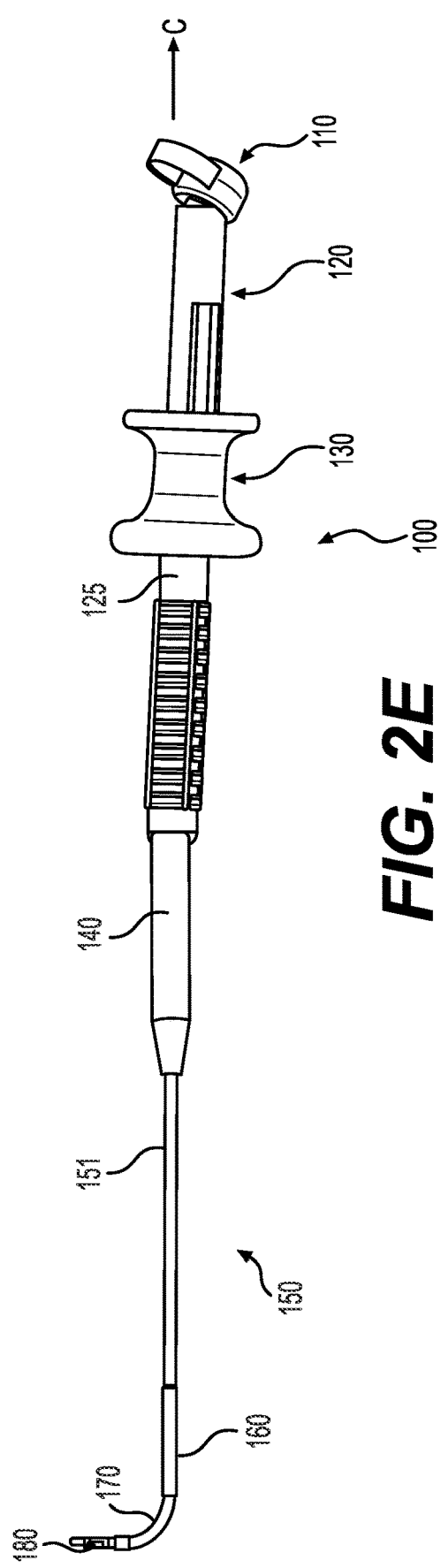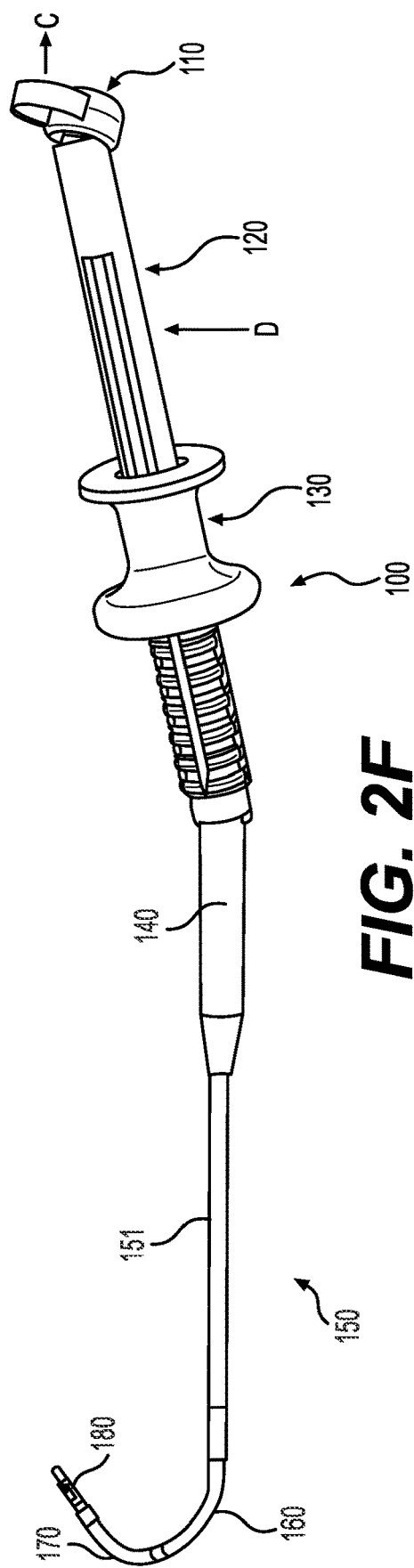
FIG. 2E
FIG. 2F

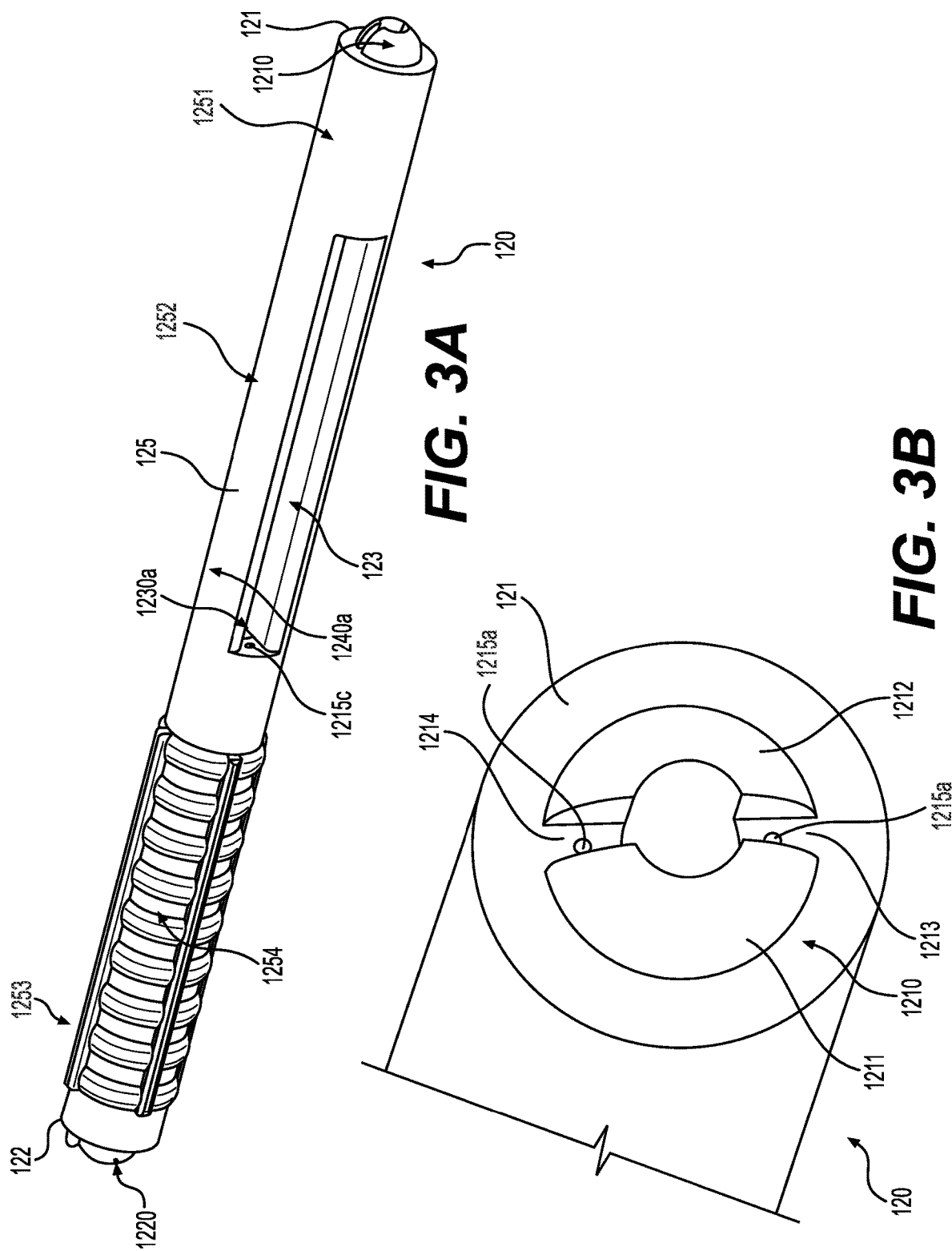

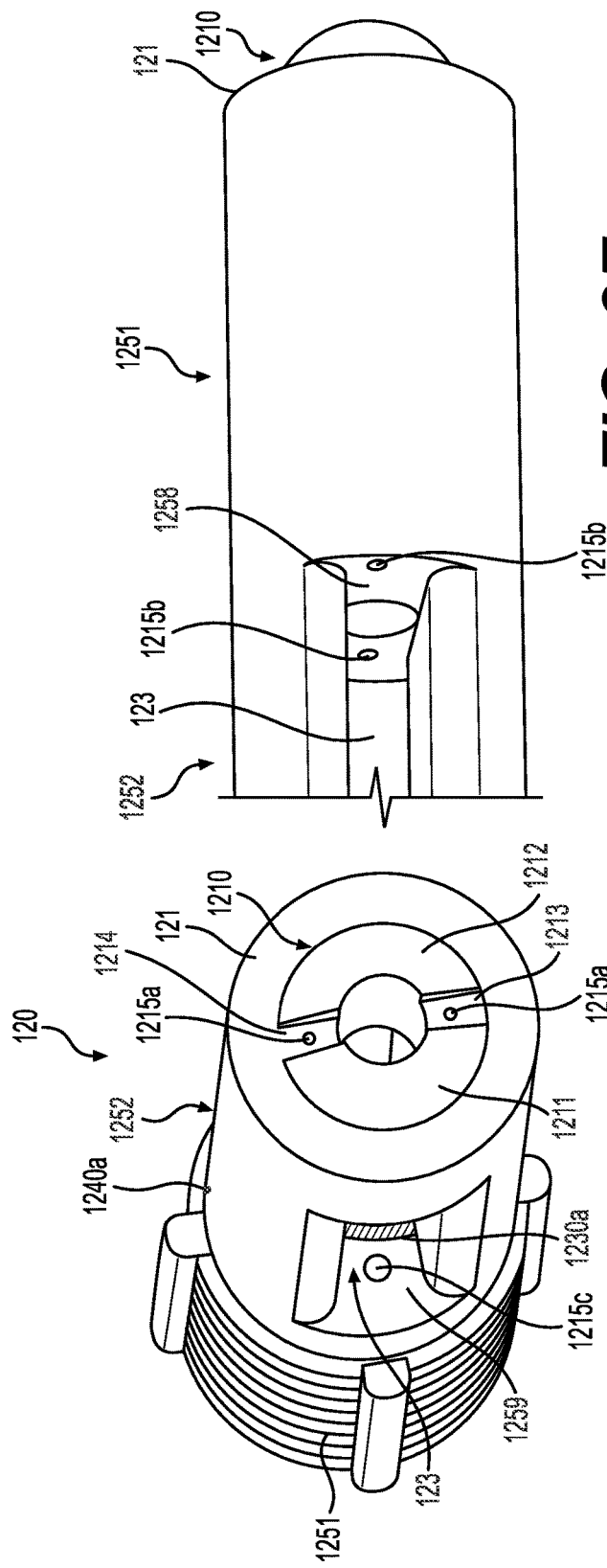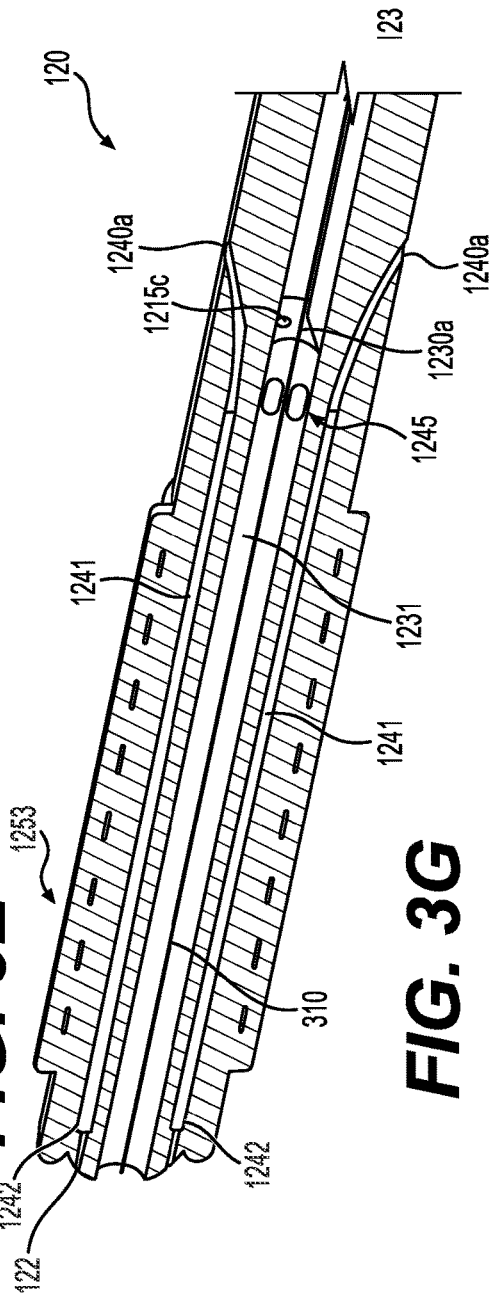

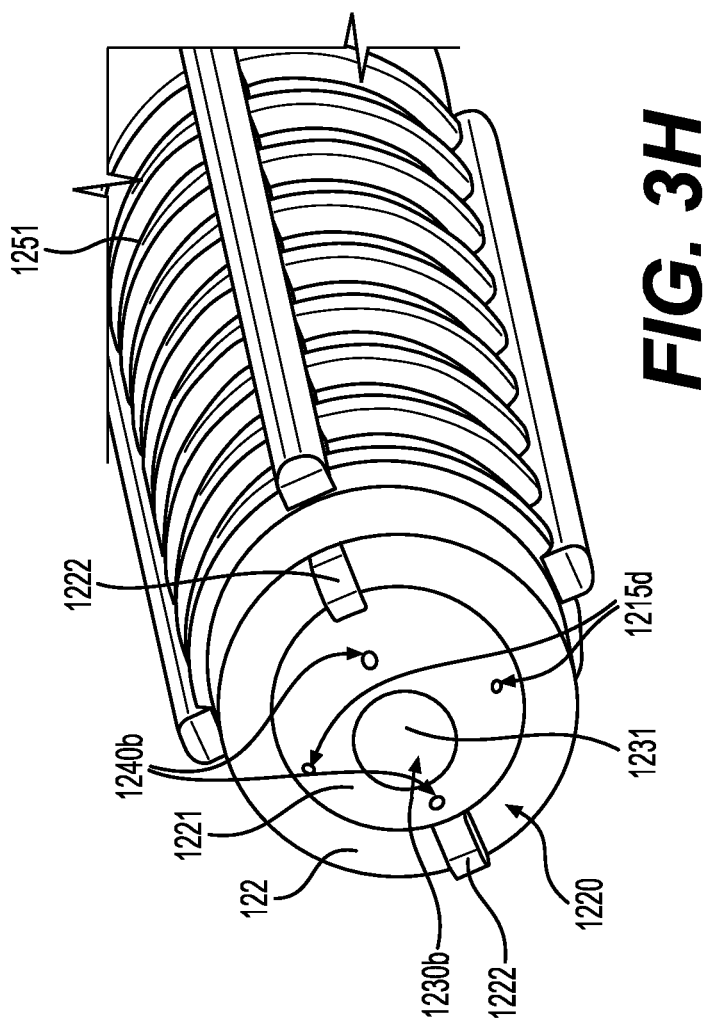

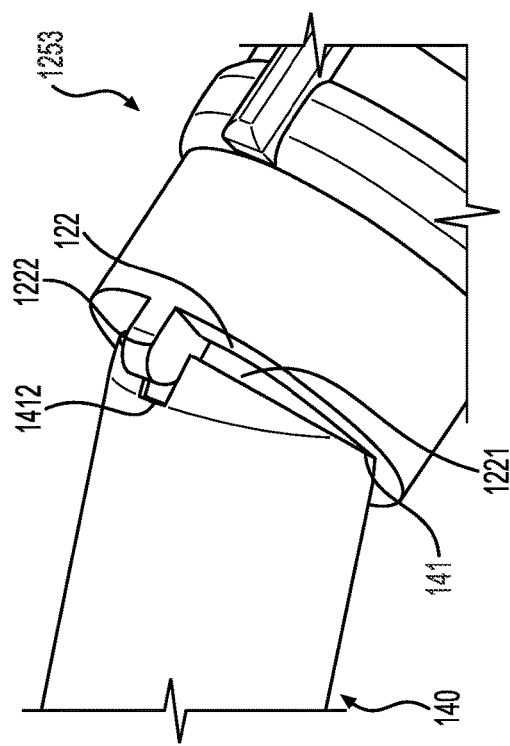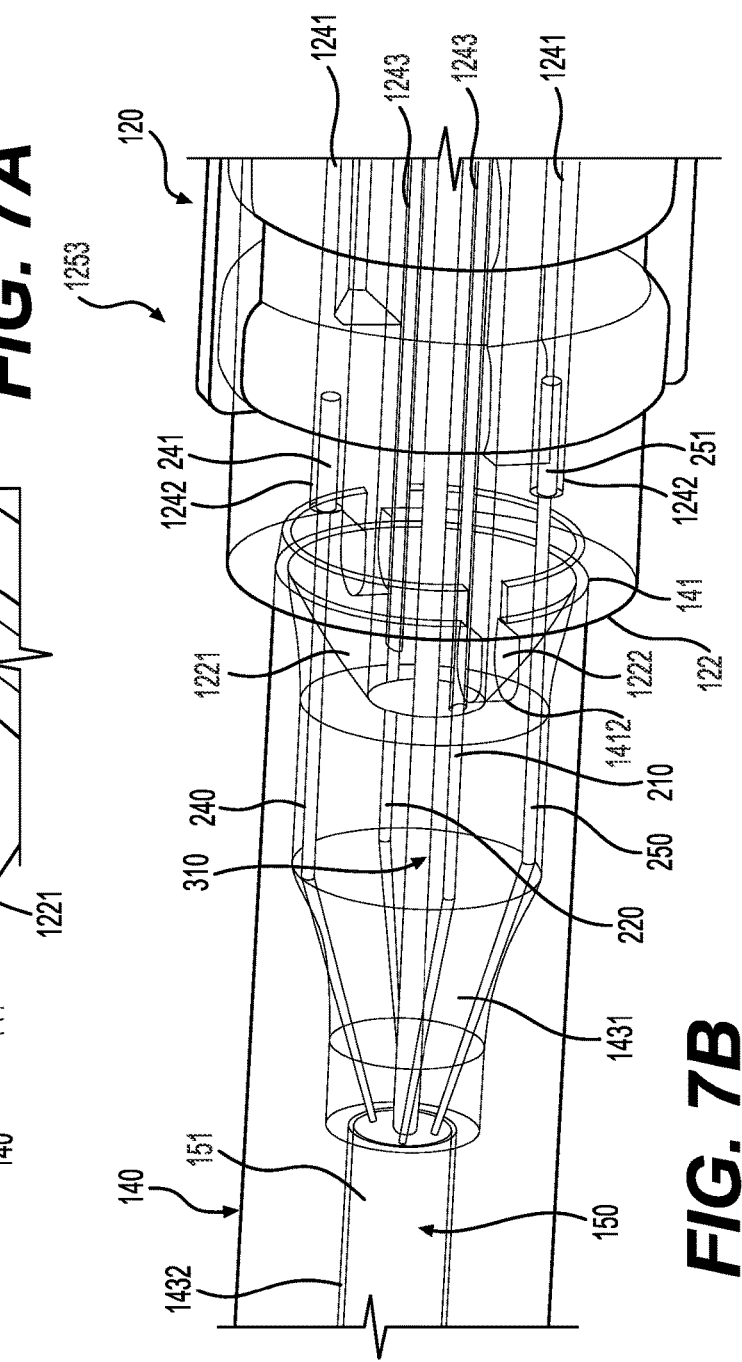

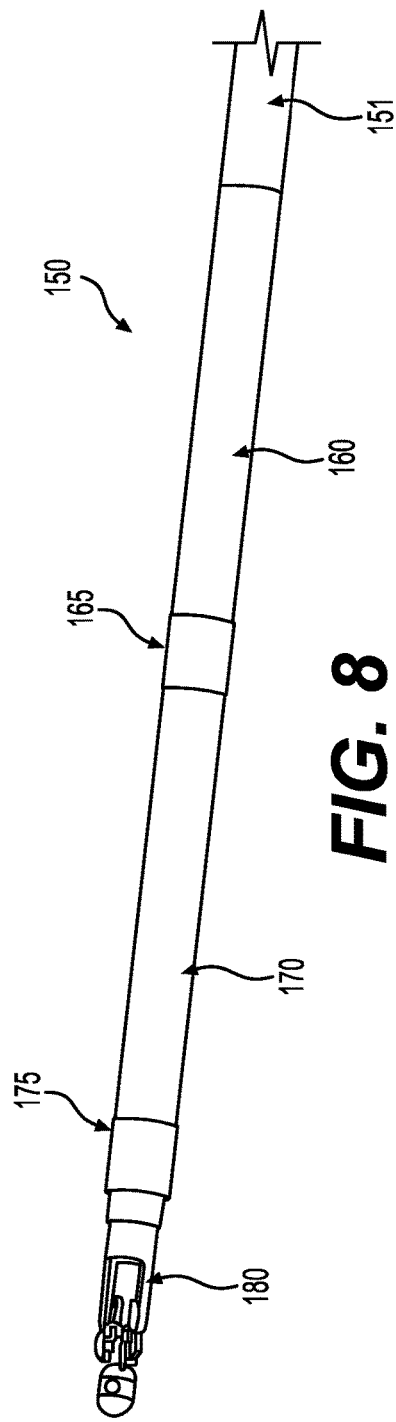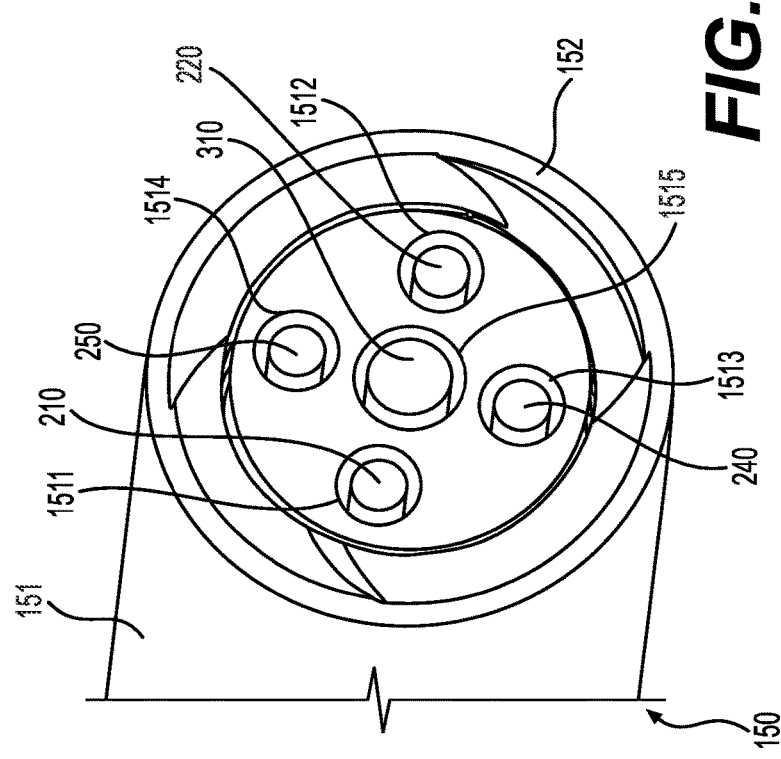

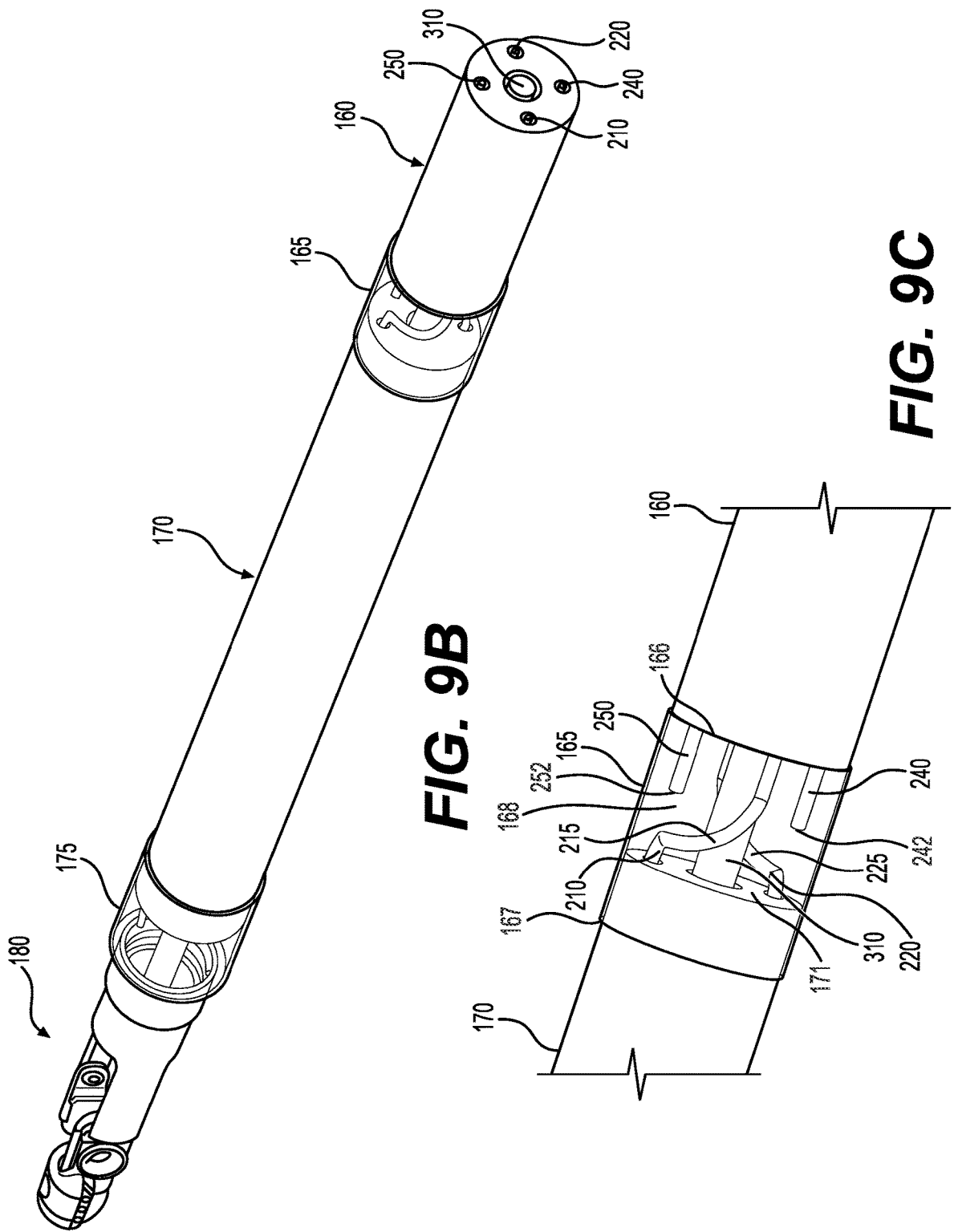

MEDICAL SYSTEMS, DEVICE, AND RELATED METHODS THEREOF

CROSS-REFERENCE TO RELATED APPLICATION(S)

This application claims the benefit of priority from U.S. Provisional Application No. 63/213,632, filed on Jun. 22, 2021, which is incorporated by reference herein in its entirety.

TECHNICAL FIELD

This disclosure relates generally to medical systems and devices. More particularly, at least some embodiments of the disclosure relate to articulable medical devices for endoluminal procedures.

BACKGROUND

In some instances, endoluminal procedures may be complex, and may involve many hands of operators or technicians working conjunctively. Thus, such procedures may require a high cognitive load. Furthermore, accessory devices commonly used may have certain deficiencies, thereby failing to alleviate the complexity and cognitive burden of such procedures. Some of the deficiencies include accessory devices lacking any independent articulation at a distal end of the devices, or devices having only a two-wire articulation in a single plane thereby failing to create enough articulating force due to limitations such as steering wire diameter and frictional losses in a tortuous anatomy. Moreover, other deficiencies may stem from the end effector features of accessory devices. For example, jaws of biopsy forceps/graspers may lack a closing force to sufficiently grab tissue, as the common 4-bar mechanism to close jaws may have a reduced mechanical advantage. Thus, current accessory devices may be complex, ineffective, and expensive.

SUMMARY OF THE DISCLOSURE

Aspects of the disclosure relate to, among other things, medical systems and devices for endoluminal procedures, among other aspects. Each of the aspects disclosed herein may include one or more of the features described in connection with any of the other disclosed aspects.

According to an example, a medical device may comprise a handle extending between a first end and a second end, a first actuator coupled to the first end of the handle, a first shaft coupled to the second end of the handle, and a second shaft extending from the first shaft, the second shaft including a first articulation section and a second articulation section, wherein an articulation of the first actuator relative to the handle is configured to articulate the first articulation section, an articulation of the handle relative to the first shaft is configured to articulate the second articulation section, and the first articulation section and the second articulation section are restricted to articulating only in a first plane.

In another example, the first actuator is configured to articulate relative to the handle within only the first plane and the handle is configured to articulate relative to the first shaft within only the first plane. The handle, the first actuator, the first shaft, and the second shaft are configured so that they must rotate together about a longitudinal axis of the medical device in unison. The first actuator is pivotably coupled to the first end of the handle so that the first actuator is configured to pivot relative to the handle within only the first plane. The second end of the handle is pivotably coupled to the first shaft so that the handle is configured to pivot relative to the first shaft within only the first plane. The second articulation section is proximal to the first articulation section.

In another example, the second shaft further includes a non-articulating section adjacent to the second articulating section, a first articulation coupler coupled to a first end of the first articulation section, and a second articulation coupler coupling a second end of the first articulation section to a first end of the second articulation section. The medical device may further comprise a first wire, a second wire, a third wire, and a fourth wire, wherein each of the first wire and the second wire includes a first end fixed within the first actuator, and each of the third wire and the fourth wire includes a first end fixed within a portion of the handle, and wherein the first wire and the second wire are configured to articulate the first articulation section, and the third wire and the fourth wire are configured to articulate the second articulation section. Each of the first wire and the second wire further includes a second end fixed within the first articulation coupler, and each of the third wire and the fourth wire further includes a second end fixed within the second articulation ring. Longitudinally-extending portions of the second ends of the first wire, the second wire, the third wire, and the fourth wire extend along a shared plane.

In another example, the medical device may further comprise an end effector and a second actuator configured to actuate the end effector, wherein the second actuator is coupled to a portion of the handle between the first end and the second end, and the second actuator is slideably coupled to the handle so that the second actuator may translate along the portion of the handle between the first end and the second end. The first shaft is coupled to the second end of the handle via a ball and socket connection. The first actuator is coupled to the first end of the handle via a ball and socket connection.

In another example, the medical device may further comprise a second actuator, wherein the first actuator and the second actuator are positioned relative to each other so that the first actuator is accessible by a first finger of a hand and the second actuator is accessible by a second finger of the hand without changing a position of the hand relative to the medical device. The handle is configured to be articulated via a flexion of the hand.

According to another example, a medical device may further comprise a handle extending between a first end and a second end, a first actuator pivotably coupled to the first end of the handle, a first shaft pivotably coupled to the second end of the handle, a second shaft extending from the first shaft, the second shaft including a first articulation section and a second articulation section, a first set of connectors between the first actuator and the first end of the handle, wherein said first set restricts a pivoting of the first actuator to a first pivot axis, and a second set of connectors between the first shaft and the second end of handle, wherein said second set restricts a pivoting of the first shaft to a second pivot axis, wherein the pivoting of the first actuator relative to the handle is configured to articulate the first articulation section and the pivoting of the handle relative to the first shaft is configured to articulate the second articulation section. The first pivot axis and the second pivot axis are co-planar. The first set of connectors includes slots and tabs received by the slots. The second set of connectors includes slots and tabs received by the slots.

According to another example, a method of positioning a shaft of a medical device may comprise inserting a distal end of a shaft of the medical device into a body of a subject, articulating a first actuator of the medical device relative to a handle of the medical device to articulate the shaft in a first direction, wherein said articulation is restricted by configuration of the medical device to a single plane, and articulating the handle relative to an intermediary shaft of the medical device to articulate the shaft in a second direction, wherein said articulation is restricted by the medical device to the single plane.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 2A-2F are perspective views of a medical device, according to some aspects of the present disclosure.

FIGS. 3A-3H are perspective and sectional views of the handle of the medical device of FIGS. 2A-2F.

FIGS. 7A-7B are sectional views of a handle and shaft portion of the medical device of FIGS. 2A-2F.

FIG. 8 is a perspective view of another shaft portion of the medical device of FIGS. 2A-2F.

FIGS. 9A-9E are perspective and sectional views of another shaft portion of the medical device of FIGS. 2A-2F.

DETAILED DESCRIPTION

Figure 1A:
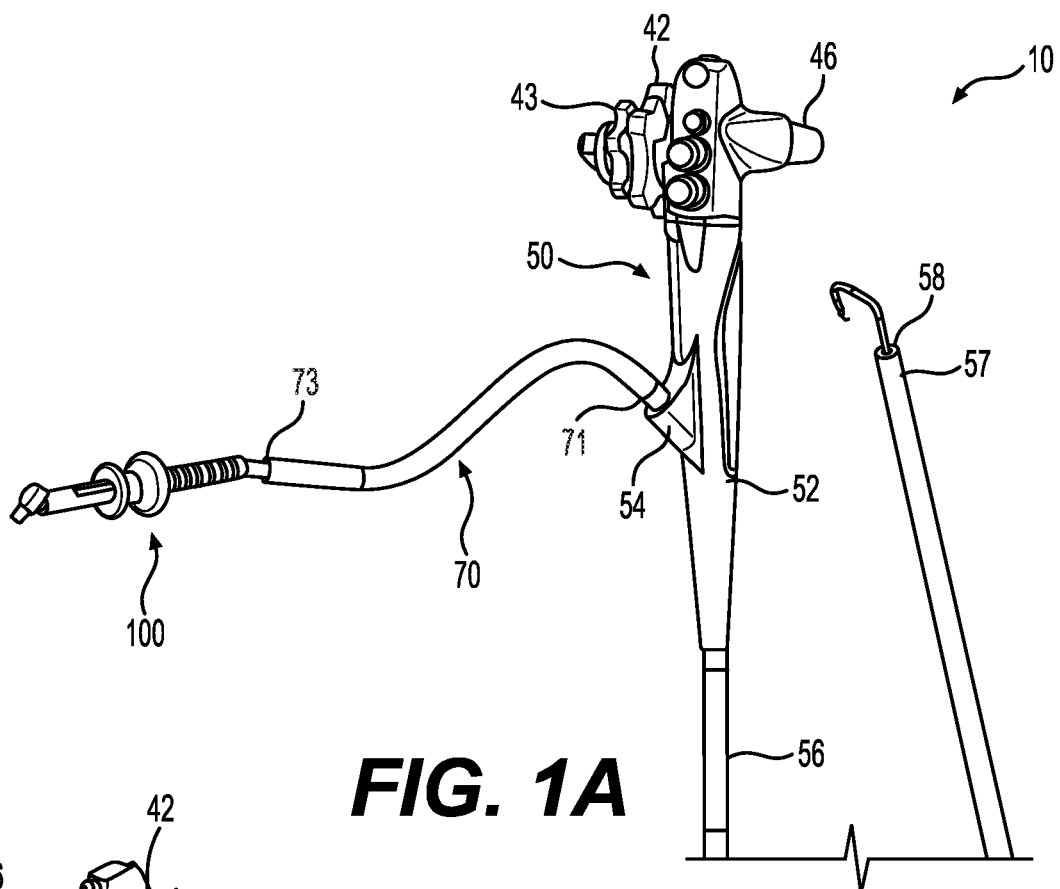
FIGS. 1A-1B are perspective views of a medical system, according to some aspects of the present disclosure.

Reference will now be made in detail to aspects of the disclosure, examples of which are illustrated in the accompanying drawings. Wherever possible, the same or similar reference numbers will be used through the drawings to refer to the same or like parts. The term "distal" refers to a location or portion of a medical device farthest away from a user of the device, e.g., when introducing a device into a subject (e.g., patient). By contrast, the term "proximal" refers to a location or portion closest to the user, e.g., when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Embodiments of this disclosure include systems, devices, and methods for performing endoluminal procedures. Exemplary systems may include a medical scope, e.g., an endoscope, a coupling device, and a medical device. The scope is not particularly limited and may be any suitable medical scope. Said medical scope may include a port configured to receive said medical device, e.g., an accessory device, via the coupling device.

The coupling device is also not particularly limited and may be any suitable tube, channel, railing, or guide including a first end and a second end, the first end configured to couple onto a port of the scope. The manner in which the first end couples onto the port is not particularly limited. The second end may include an opening or a passage leading to a lumen or a channel configured to guide the medical device towards an opening of said port. The coupling device may provide stability to the connection between the medical device and the scope. The coupling device may further include a locking mechanism to further secure the connection to the medical device. The coupling device may also provide a surface that a shaft portion of the medical device may press against, when the handle portion is pivoted relative to the shaft, thereby actuating a secondary articulation mechanism of the medical device (discussed in further detail below). Thus, the coupling device may serve as a fulcrum for said secondary articulation. The length of the coupling device may be any suitable length accommodating the medical device. The shape of the coupling device may be any suitable shape assisting with the ergonomics of the medical system.

The medical device may be an accessory device configured to be utilized in conjunction with a medical scope. The medical device may be inserted into a port of the scope, via the coupling device discussed above. The medical device may extend longitudinally from a first, proximal end to a second, distal end. The medical device may include a handle, a first actuator pivotably coupled to a proximal end of the handle, a second actuator coupled to a body of the handle, an intermediary shaft pivotably coupled to a distal end of the handle, a main shaft extending distally from said intermediary shaft, the main shaft including a non-articulating portion, first articulating portion and a second articulating portion, and an end effector coupled to a distal end of the main shaft. The medical device may further include a first pair of primary steering wires, a second pair of secondary steering wires, and a pull wire configured to actuate the end effector.

It is noted that the main shaft is not particularly limited, and may be any suitable multi-lumen shaft. For example, the main shaft, e.g., the non-articulating portion, first articulating portion, and second articulating portion, may comprise at least a PTFE body defining a plurality of lumens. The number of lumens may vary in each portion of the shaft. In other examples, the shaft may further comprise a braiding and/or a coil over said PTFE body configured to provide stiffness and torquability. The braiding/coil is not particularly limited and may be round or flat. Said coil may be a dual layer or a triple layer wire wounded in any direction. The braiding may be of a diamond, regular or Hercules pattern. An outer covering of portion of the shaft is also not particularly limited, and may be any suitable material, e.g., a FEP reflow, configured to maintain said multi-lumen shaft and braiding. It is noted that a secondary reflow may be included beneath said braiding for improved torque of the shaft. Moreover, said main shaft may be compatible with typical working channels, e.g., 2.8 mm, of medical scopes.

The steering wires of the medical device are also not particularly limited, and may be any suitable steering wire. In some examples, the steering wires made include stainless steel with a silicon coating, e.g., MDX coating. The steering wires may be of a single strand or a multi strand wire. Furthermore, the steering wires may be coated with any suitable material, e.g., silicon, PTFE, a lubricant, etc. Likewise, the pull wire is not particularly limited as well. The pull wire may include SS, Nitinol with MDX, PTFE, or a silicon coating. The pull wire may also be a single or multi strand wire.

The aforementioned features of the medical device are discussed in further detail when referring to the figures.

Said medical device may be a single hand held device having a number of degrees of freedom, all of which are operable via a single hand. For example, a first degree of freedom may be the articulation of the main shaft at a first articulating portion via actuation of the first actuator of the device (e.g., the primary articulation mechanism). The primary articulation mechanism may be performed via a movement of the thumb of the hand. A second degree of freedom may be the articulation of the main shaft at a second articulating portion via the pivoting of the handle relative to the intermediary shaft (e.g., the secondary articulation mechanism). The secondary articulation mechanism may be performed via a movement of the wrist of the hand. In some examples, the first articulating portion and the second articulating portion may articulate in the same direction along the same plane. This may provide an extra lift and a tighter articulating radius of the main shaft. This double-articulation may be achieved by two different pairs of steering wires lying on a shared plane at the first articulating portion and the second articulating portion of the shaft. Such a wire arrangement is described in further detail below.

A third degree of freedom may be the rotation of the shaft in a clockwise or a counterclockwise direction. As discussed in further detail below, each of the aforementioned aspects of the device may be coupled to one another so that they rotate simultaneously relative to the other aspects of the device. In other words, a rotation of a single feature, e.g., the handle, simultaneously rotates with certain other features of the device. Thus, said rotation of the shaft may be performed via a rotation of the wrist and/or forearm of the hand holding the handle. A fourth degree of freedom may be the actuation of the end effector via actuation of the second actuator. Said actuation may be performed via the movement of at least one finger of the hand holding the device. A fifth degree of freedom may be the proximal-distal translation of the medical device within a bodily lumen, which may be effectuated via a translation of the hand while holding the handle of the device.

It is noted that each of the degrees of freedom discussed above may be performed with minimal movement of the single hand along or relative to the handle of the device (relatively short/simple movements of the fingers and/or the wrist of the hand operate the medical device). Thus, the exemplary medical device discussed above may alleviate cognitive load by being fully operational via a single hand. Moreover, the device may be easy to use as it offers an intuitive interface for operating the various degrees of freedoms of the device, all of which are accessible via the movement of the fingers and/or the wrist of the single hand. The handle of the medical device may be able to be grasped by a wide range of hand sizes (small, medium, large). Furthermore, the medical device may be of low cost and disposable after use.

Figure 1B:
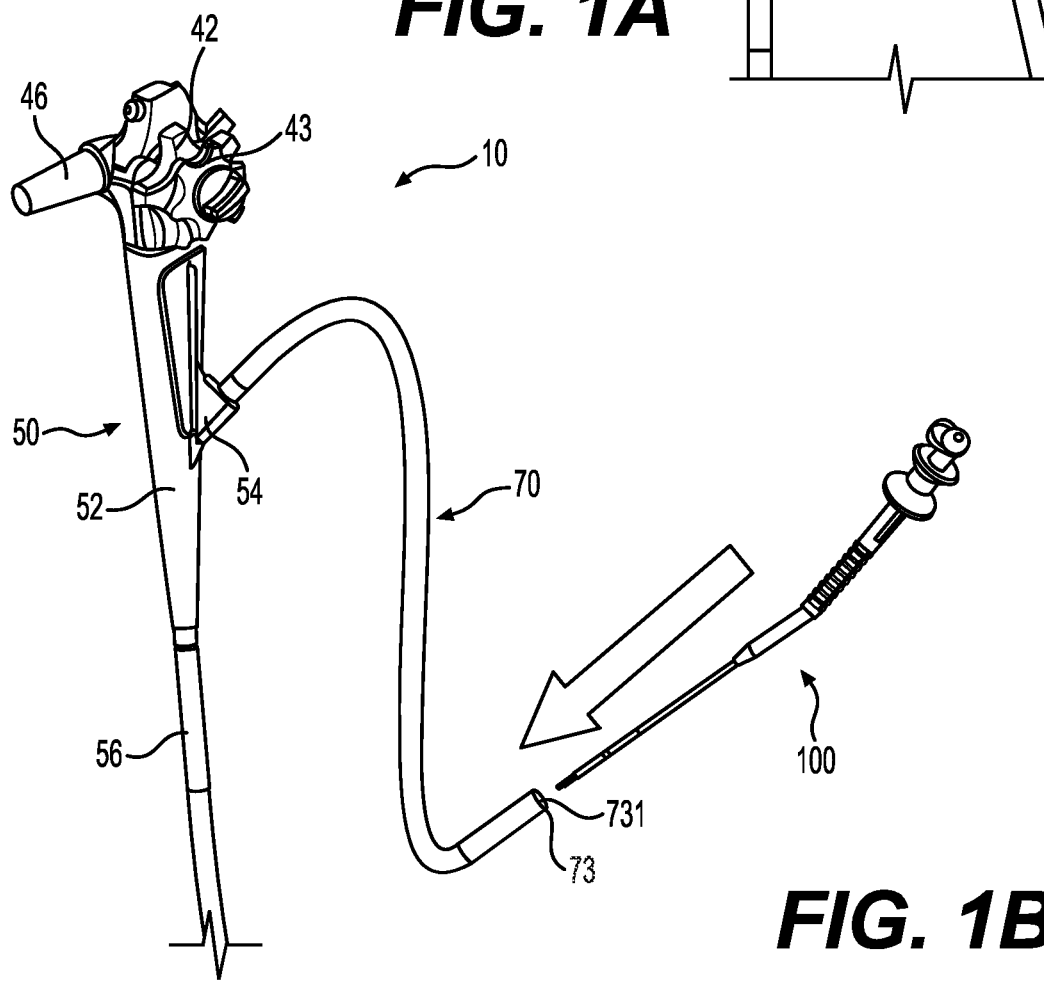

Referring to FIGS. 1A and 1B, an exemplary medical system 10 includes a scope 50, e.g., an endoscope, a coupling device 70, and a medical device 100. Scope 50 includes a flexible shaft 56 (e.g., a catheter) and a handle 52 connected at a proximal end of flexible shaft 56. Handle 52 may be configured for actuating or otherwise controlling features of medical system 10 and/or one or more tools or devices associated with medical system 10. The handle 52 as shown includes first and second actuators 42, 43, which control articulation of shaft 56, e.g., an articulation joint at or proximate a distal end of shaft 56. For example, the actuators 42, 43 may control movement of the shaft 56 in multiple directions, e.g., movement along different planes. Actuators 42, 43, may include, for example, rotatable knobs that rotate to push/pull cables or wires coupled to the shaft 56. For example, one or more cables or wires may comprise medical grade plastic or metal, and may extend distally from a respective actuator 42, 43 to connect to flexible shaft 56 to control movement thereof. Distal ends of the cables or wires may extend through shaft 56 and terminate at an articulation joint and/or a distal tip of shaft 50. For example, one or more cables or wires may be connected to an articulation joint, and rotation of actuators 52, 53 may control the cables or wires to move the articulation joint and/or the distal end of shaft 56, e.g., along multiple directions. According to some aspects of the present disclosure, one or more electrical cables (not shown) may extend from the proximal end of system 10 to the distal end of shaft 56 and may provide electrical controls to imaging, lighting, and/or other electronics at the distal end of shaft 56. Electrical cables may carry imaging signals received at the distal end of shaft 56 to be processed and/or displayed on a display. The endoscope may also include at least one port, e.g., port 54, being shown in the example of FIGS. 1A-1B, for introducing a device 100 via a coupling device 70.

As shown in FIGS. 1A-1B, coupling device 70 is a device that is tubular, but not limited thereto, extending between a first end 71 and a second end 73. First end 71 includes an opening (not shown) configured to engage or couple with port 54 so that an entrance of port 54 (not shown) and said opening of first 71 are in fluid communication and otherwise permit materials to travel between scope 50 and coupling device 70. The manner in which first end 71 couples to port 54 is not particularly limited, and may be via any suitable manner or mechanism, e.g., adhesive, engageable threading, locking component, etc. Second end 73 may include an opening 731 (shown in FIG. 1B) configured to receive a distal portion of device 100. Thus, device 100 may traverse a channel (not shown) extending between opening 731 and said opening of first end 71 to enter port 54, and extend distally along a working channel of shaft 56 of scope 50. As shown in FIGS. 1A-1B, coupling device 70 may be a curved, S-shape structure, which may provide an ergonomic benefit to an operator when using system 10. However, it is noted that the shape and length of device 70 is not particularly limited, and may be any suitable length and/or shape. Device 70 may be flexible enough to permit changes to the configuration, but may be configured with sufficient rigidity to maintain the new shapes.

FIGS. 2A-2B illustrate medical device 100, shown in FIGS. 1A-1B. Medical device 100 includes a handle 120, a first actuator 110 that is pivotably coupled to a proximal end of handle 120, a second actuator 130 slidably coupled to a body 125 of handle 120, an intermediary shaft 140 that is pivotably coupled to a distal end of handle 120, a main shaft 150 extending distally through and from within said intermediary shaft 140, the main shaft including a first articulating portion 170 and a second articulating portion 160 that is proximal to portion 170, and an end effector 180 coupled to a distal end of main shaft 150. Further detail with respect to each of the aforementioned features of device 100 is discussed in further detail below.

Handle

Referring to FIG. 3A, a handle 120 is shown. As can be seen, handle 120 is a tubular-shaped structure. However, the shape of handle 120 is not particularly limited, and in some embodiments, may have a more defined, edged structure. Handle 120 includes a proximal end 121, a body 125, and a distal end 122. Proximal end 121 includes a proximal coupling portion 1210 configured to engage with first actuator 110 (shown in FIG. 2A). Body 125 includes a longitudinally extending recess 123 facing radially outward and configured to receive a portion of second actuator 130 (shown in FIG. 2A), and further includes a corrugated portion 1254. Distal end 122 includes a distal coupling portion 1220 configured to engage with intermediary shaft 140 (shown in FIG. 2A).

A more detailed description of proximal end 121 of handle 120 and proximal coupling portion 1210 is provided below. As shown in FIG. 3B, proximal coupling portion 1210 is centrally located on proximal end 121. Proximal coupling portion 1210 includes protrusions 1211 and 1212, slots 1213 and 1214, both of which are between protrusions 1211 and 1212, and wire openings 1215a which reside within slots 1213 and 1214. Each of protrusions 1211 and 1212 are C-shaped, half-moon, or partial-ring like protrusions having two ends. Protrusions 1211 and 1212 mirror each other so that the ends of protrusion 1211 face the ends of protrusion 1212. Protrusions 1211 and 1212 protrude proximally relative to the surface of proximal end 121. Thus, protrusion 1211 and protrusion 1212 form a partial ball/sphere like structure, configured to mate with a spherical cavity 1152 of actuator 110 (shown in FIG. 3B). Excluding protrusions 1211 and 1212, the remaining proximally-facing surface of proximal end 121 may otherwise be flat so it may be placed flush against the flat portions of a distal facing surface of first actuator 110, as discussed in further detail below.

Figure 3C:
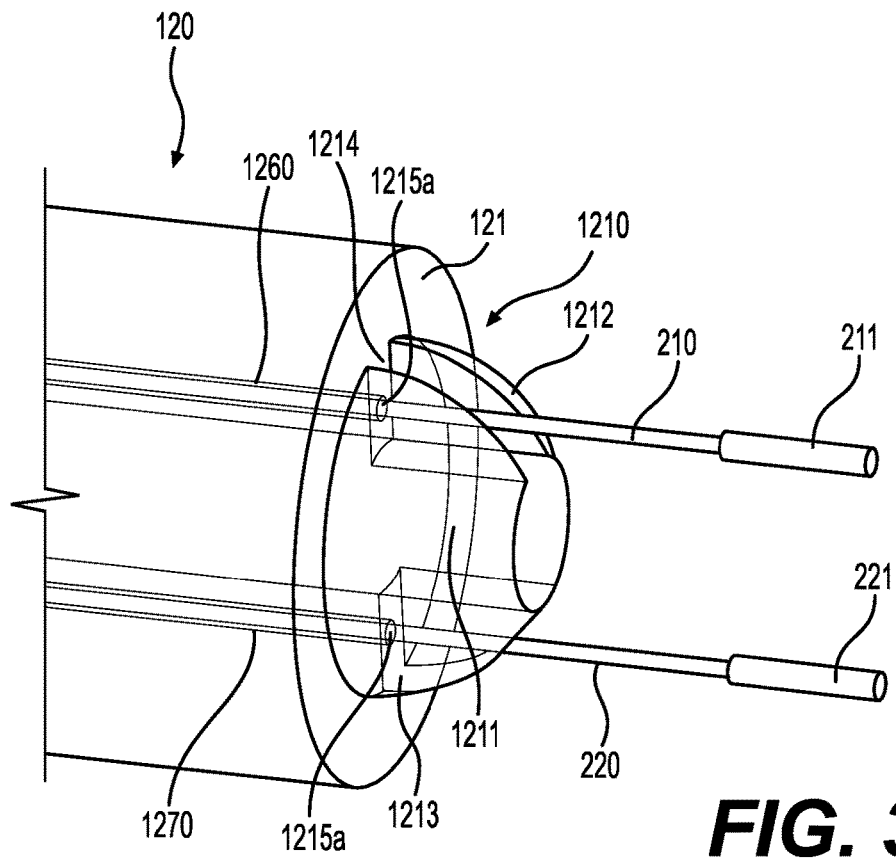

Slots 1213 and 1214 are partially-defined by the surface of proximal end 121 in between the respective ends of protrusions 1211 and 1212. Slots 1213 and 1214 may be dimensional to receive tabs 1153 and 1154 of first actuator 110 (shown in FIG. 4A). Slots 1213 and 1214 each including a wire opening 1215a, configured to receive primary steering wires 210/220, as shown in FIG. 3C. Wire openings 1215a are co-planar. The positioning of openings 1215a within slots 1213 and 1214 is such that openings 1215a may align with wire openings 160 of first actuator 110 (shown in FIG. 4A), as discussed in further detail below.

A more detailed description of body 125 of handle 120 is provided below. As shown in FIG. 3A, body 125 extends between proximal end 121 and distal end 122. Body 125 includes a proximal portion 1251, a mid portion 1252 including recess 123, and a distal portion 1253 including a corrugated outer surface 1254. In addition, it is noted that body 125 includes a plurality of openings and channels configured to provide passage for primary steering wires, e.g., steering wires 210, 220, and a pull wire, e.g., wire 310, to extend throughout the length of body 125.

Figure 3D:
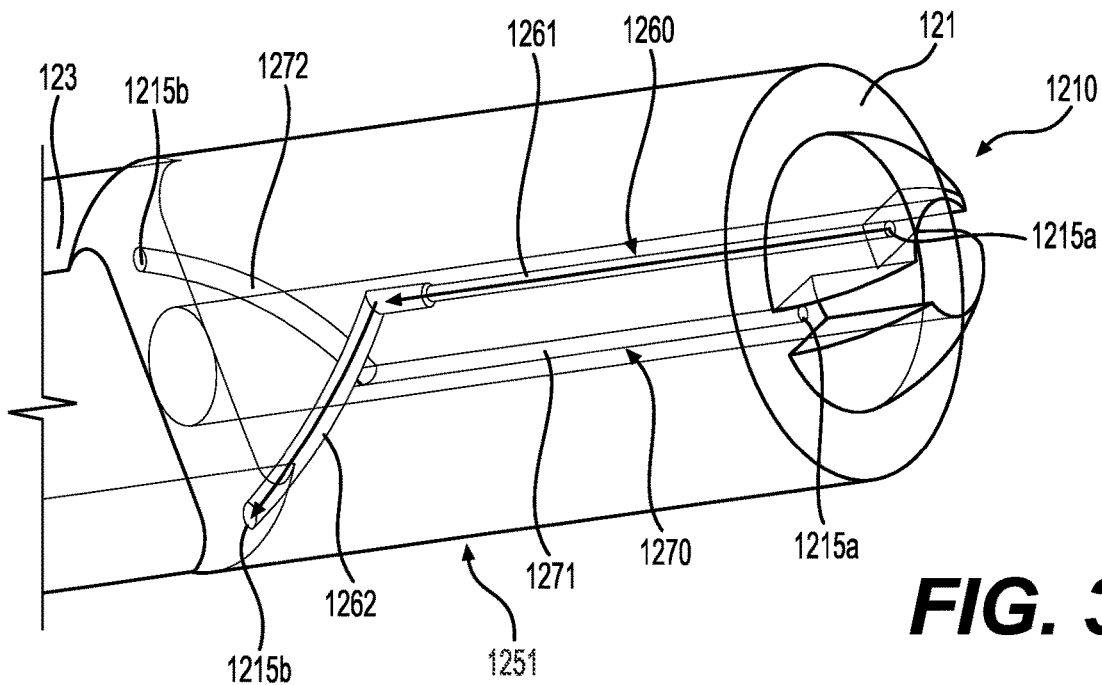

Referring to FIGS. 3C and 3D, a sectional view of the proximal portion 1251 of body 125 is shown. In addition to proximal coupling portion 1210, proximal portion 1251 includes a wire channel 1260, a wire channel 1270, and wire openings 1215b. As shown, wire openings 1215a of proximal coupling portion 1210 lead to wire channels 1260 and 1270, which are configured to receive and house steering wires 210, 220 (discussed in further detail below). Wire channels 1260 and 1270 extend distally within proximal portion 1251 of body 125. Each of wire channels 1260 and 1270 respectively include a proximal, first section 1261, 1271 and a distal, second section 1262, 1272. First sections 1261 and 1271 extend distally from openings 1215a in a straight-line, linear fashion, as indicated by the directional arrow. As they extend, first sections 1261 and 1271 transition to second sections 1262 and 1272. As shown in FIG. 5B, second sections 1262 and 1272 curve at an angle (as indicated by the directional arrow), relative to first sections 1261, 1271, towards distal wire openings 1215b. Distal wire openings 1215b are oriented 90°, or approximately 90°, relative to the orientation of openings 1215a. It is noted that first section 1261 and second section 1262 and first section 1271 and second section 1272 may be of single, unitary channels, or may be two individual channel sections joined together as shown in FIG. 3D. Thus, channels 1260 and 1270 define a path for primary steering wires 210, 220 to extend through openings 1215a of coupling portion 1210 to openings 1215b which lead to recess 123 of mid portion 1252 as shown in FIG. 3E.

Referring to FIGS. 3A, 3E, and 3F, mid portion 1252 is further discussed. Mid portion 1252 refers to the portion of body 125 including recess 123. Recess 123 extends between a proximal surface 1258 and a distal surface 1259. Recess 123 defines a longitudinal slot configured to receive a portion of second actuator 130. Moreover, recess 123 is shaped and sized so as to allow said portion of second actuator 130 to slidably translate within recess 123, while also frictionally engaging said portion so that second actuator 130 may maintain its position along body 125. The engagement between second actuator 130 and recess 123 is further discussed below, when referring to FIGS. 5A-5B. As shown in FIGS. 3E-3F, surface 1258 includes two wire openings 1215b, and surface 1259 includes two wire openings 1215c (only one is shown) and a central opening 1230a. Each wire opening 1215b may be aligned with a wire opening 1215c so that each primary steering wire 210, 220 may extend through an opening 1215b to an opening 1215c, in a straight, linear manner. Thus, steering wires 210, 220 may extend distally from wire openings 1215b, throughout recess 123, into openings 1215c, which transition to primary steering wire channels 1243 (shown in FIG. 7B). It is noted that steering wires 210, 220 may pass through second actuator 130 via through holes (not shown) extending throughout second actuator 130. Central opening 1230a leads to a central lumen 1231 of distal portion 1253, and is configured to receive a pull wire, e.g., a wire 310, that extends between second actuator 130 and end effector 180, as discussed further below. Central opening 1230a is configured to accommodate for the longitudinal translation of said pull wire, e.g., wire 310, through opening 1230a.

As shown in FIGS. 3E-3G, mid portion 1252 may further include two openings 1240a along an outer circumferential surface of mid portion 1252. Openings 1240a may lie along a distal portion of portion 1252, and may extend in a plane that is perpendicular to the plane on which openings 1215c extend. Openings 1240a transition to channels 1241 which extend distally towards a distal end of body 125. Thus, openings 1240a may be configured to receive a second set of steering wires, e.g., steering wires 240 and 250 (shown in FIG. 7B), which may extend distally through distal portion 1253 of body 125 via channels 1241. It is noted that, in some embodiments, body 125 may be without openings 1240a, and that during the manufacturing process of device 100, steering wires 240 and 250 may be installed and fixed within distal portion 1253 of body 125 without requiring openings 1240a.

Referring to FIGS. 3A and 3G, distal portion 1253 of body 125 is discussed in further detail. As shown in FIG. 3A, an outer surface of distal portion 1253 includes corrugated portion 1254, which may provide better handling and grip of distal portion 1253 of handle 120. However, it is noted that distal portion 1253 may be without corrugation portion 1254, or may substitute corrugated portion 1254 for a different feature that may assist with the handling and grip of handle 120. As shown in FIG. 3G, distal portion 1253 further includes two wire channels 1241 for secondary steering wires 240, 250 (shown in FIG. 7B), two wire channels 1243 (shown in FIG. 7B) for primary steering wires 210, 220 (shown in FIG. 7B), a central lumen 1231 for wire 310, and a winding mechanism 1245, e.g., a pulley, fixed within lumen 1231.

Wire channels 1241, for secondary steering wires 240, 250, extend distally from openings 1240a towards distal end 122. More specifically, channels 1241 curve radially inwards, before extending longitudinally along and substantially parallel to central lumen 1231. Wire channels 1243, for primary steering wires 210, 220, also extend distally from openings 1215c towards distal end 122 (shown in FIG. 7B). Channels 1243 may extend in a straight, linear manner throughout their lengths, so that channels 1243 run parallel (or about parallel) to central lumen 1231.

Central lumen 1231 is centrally located within distal portion 1253, around the longitudinal axis of handle 120. Lumen 1231 extends distally from opening 1230a of surface 1259 to distal end 122. The dimensions of lumen 1231 are not particularly limited, so long as lumen 1231 may accommodate for the translation of pull wire 310. Central lumen 1231 may also house winding mechanism 1245, as shown in FIG. 3G. Winding mechanism 1245 is not particularly limited, and may be any suitable pulley-like device. Winding mechanism 1245 may be fixedly coupled within lumen 1231. The manner by which winding mechanism 1245 is fixed to body 125 within lumen 1231 is not particularly limited. As shown, winding mechanism 1245 may receive wire 310. Wire 310 may wrap around winding mechanism 1245 as wire 310 enters lumen 1231, and continue to extend distally towards distal end 122. In some examples, wire 310 may be lubricated to more smoothly engage with winding mechanism 1245. By such configuration, winding mechanism 1245 may provide an increased mechanical advantage at a proximal portion of wire 310, so that more force may be transferred to a distal portion of wire 310, which is coupled to end effector 180. For example, said increased mechanical advantage may improve the grasping force of a grasping end effector 180, e.g., forceps. It is noted that mechanism 1245 is not particularly limited to a pulley, but may be other suitable mechanisms configured to increase the mechanical advantage of a proximal portion of wire 310.

Referring to FIG. 3H, a more detailed description of distal end 122 of handle 120 and distal coupling portion 1220 is provided below. Distal end 122 includes a distal coupling portion 1220 centrally located on distal end 122, and two tabs 1222 at the outer periphery of coupling portion 1220. Excluding distal coupling portion 1220 and tabs 1222, the surface of distal end 122 may otherwise be flat, as shown in FIG. 3H. Distal coupling portion 1220 includes a protrusion 1221, an opening 1230b, two wire openings 1215d, and two wire openings 1240b. Protrusion 1221 is a circular/annular shaped protrusion that protrudes distally relative to a flat surface of distal end 122. Thus, protrusion 1221 may define a partial ball/sphere like structure, configured to mate with a receiving end of intermediary shaft 140. However, it is noted that protrusion is not limited to a particular shape, and may be any suitable protrusion configured to engage with a receiving end of intermediary shaft 140.

Protrusion 1221 includes an opening 1230b centrally located on protrusion 1221. Opening 1230b is in fluid/material communication with central lumen 1231 and opening 1230a of handle 120, thereby permitting materials to travel through opening 1230a and 1230b. Thus, opening 1230b may be configured to accommodate for the translation of wire 310 through opening 1230b. Protrusion 1221 further includes two openings 1215d, through which primary steering wires, 210, 220, may extend distally, and two openings 1240b, through which second steering wires, 240, 250, may extend distally. Openings 1215d and 1240b are disposed on protrusion 1221, surrounding central opening 1230b. It is noted that openings 1215d are positioned diametrically across from each another, and likewise, openings 1240b are positioned diametrically across from each other. Openings 1215d and openings 1240b alternate circumferentially on protrusion 1221. Thus, openings 1215d and openings 1240b, while surrounding central opening 1230b, may be arranged so that each of the distances between an opening 1215d and an opening 1240b are equal. Moreover, it is noted that opening 1215d and openings 1240b are disposed in the same plane—a plane perpendicular to a longitudinal axis of handle 120.

As noted above, distal end 122 further includes two tabs 1222 positioned radially outward of coupling portion 1220. However, it is noted that the number of tabs surrounding coupling portion 1220 is not particularly limited. Tabs 1222 protrude distally relative the flat surface of distal end 122, and are configured to engage with a receiving end of intermediary shaft 140. As shown, tabs 1222 may be positioned diametrically across from one another. It is noted that tabs 1222 may be positioned along the same plane as slots 1213 and 1214 of proximal end 121. This is so that first actuator 110 coupled to proximal end 121 and intermediary shaft 140 coupled to distal end 122 may also pivot, relative to handle 120, along the same plane.

First Actuator

Figure 4A:
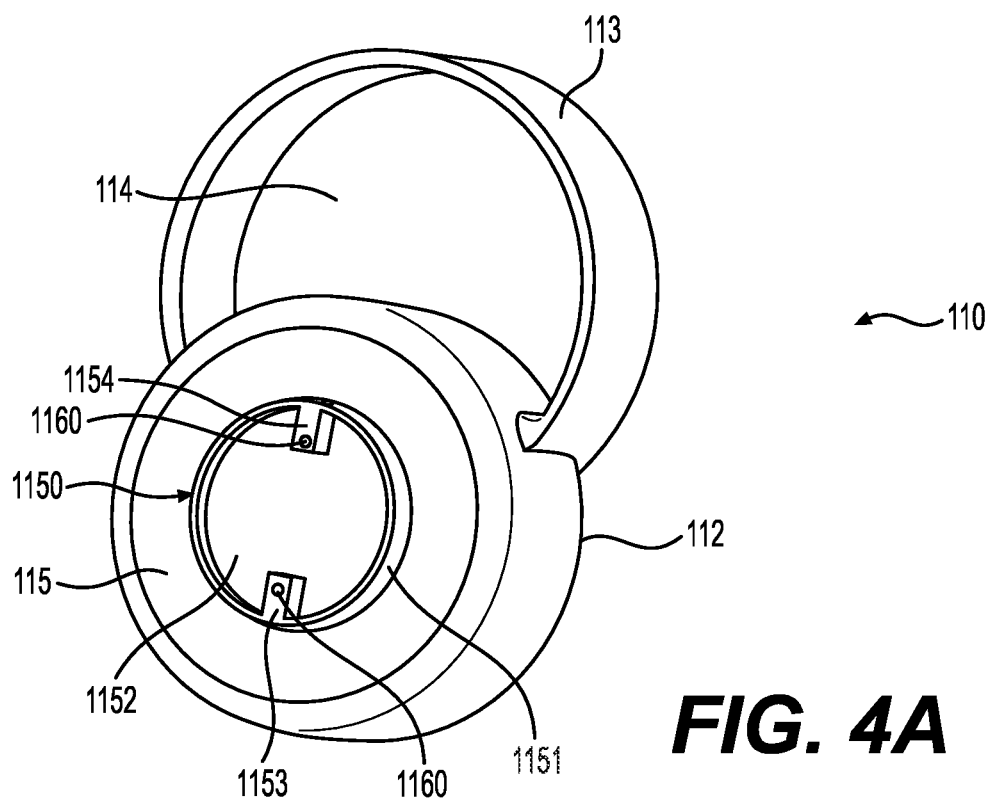
FIGS. 4A-4B are perspective views of an actuating feature of the medical device of FIGS. 2A-2F.

Referring to FIG. 4A, a first actuator 110 is shown. First actuator 110 includes a body 112, a ring 113 coupled to body 112, thereby defining an opening 114. Body 112 is spherical or partially spherical (as shown in FIG. 2A), but not limited thereto. As shown in FIG. 4A, body 112 includes a distal surface 115 that includes a coupling portion 1150 configured to engage a proximal end 121 of handle 120. Besides coupling portion 1150, distal surface 115 may otherwise be flat so it may be placed flush against the flat portions of proximal end 121.

Coupling portion 1150 includes a distally protruding fencing or outline 1151 that defines at least a portion and a circumference of partially spherical cavity 1152, and further includes a first tab 1153 and a second tab 1154. As noted, at least a portion of cavity 1152 may be defined by fencing 1151. Cavity 1152 may also extend proximally within body 112, relative to distal surface 115. Thus, cavity 1152 may extend from fencing 1151 to a portion of body 112 that is proximal to distal surface 115. Cavity 1152 is not particularly limited and may be of any suitable dimension to receive the proximally protruding protrusions 1211, 1212 of proximal end 121 of handle 120.

Both first tab 1153 and second tab 1154 protrude radially inwards from an inner surface of fencing 1151. First tab 1153 and second tab 1154 may be diametrically across from one another. As shown, tabs 1153 and 1154 are rectangular in shape. However, the dimensions and shape of tabs 1153 and 1154 are not particularly limited, so long as said tabs may engage with or otherwise received in slots 1213, 1214 of the proximal end of handle 120. Tabs 1153 and 1154 each comprise a proximally facing surface including a wire opening 1160, which is configured to accommodate steering wire 210/220. The positioning of openings 1160 along the proximally facing surfaces of tabs 1153 and 1154 is such that openings 1160 align with wire openings 1215a of proximal end 121 of handle 120.

Ring 113 is coupled to a surface of body 112. Ring 113 may include a first end coupled to body 112, a second end also coupled to body 112, and a loop/curved structure extending between said first and second ends. Thus, ring 113 may define an opening 114 between an outer surface of body 112 and an inner surface of said loop/curved structure of ring 113. Opening 114 may be configured to receive a finger of a hand, e.g., a thumb. Ring 113 may be engageable by a finger of a hand, e.g., the thumb, and provides a surface against which the finger may rest. Ring 113 may also provide a surface for the finger to press against or pull on, thereby pulling on steering wires 210 and 220 and actuating the primary articulation mechanism, as discussed in further detail below. However, it is noted that first actuator 110 may be with or without ring 113, and that a structure of any other suitable shape may take the place of ring 113, e.g., a tab, ball, etc.

Figure 4B:
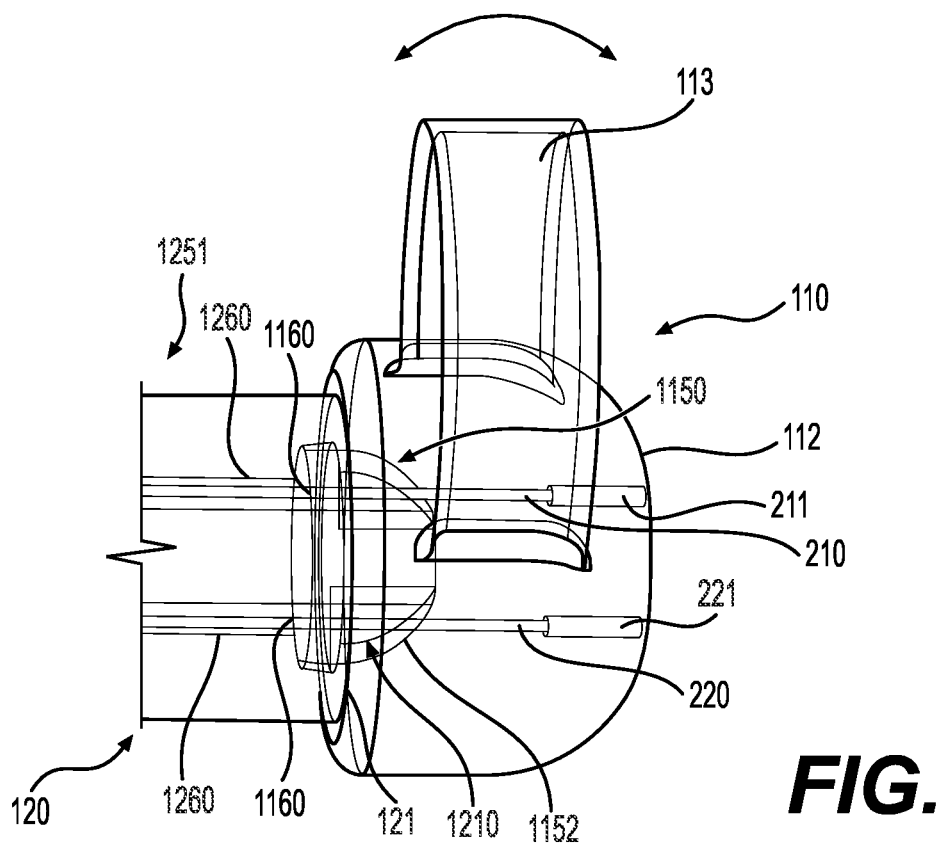

A proximal portion of device 100 including first actuator 110 coupled to proximal end 121 of handle 120, and steering wires 210, 220 is shown in FIG. 4B. First actuator 110 is pivotably coupled to proximal end 121 of handle 120 (as indicated by the directional arrow shown in FIG. 4B). This is done by coupling portion 1150 of actuator 110 engaging proximal coupling portion 1210 of handle 120. More specifically, cavity 1152 of coupling portion 1150 may receive protrusions 1211, 1212 of coupling portion 1210. For example, cavity 1152 and protrusions 1211, 1212 may be snap-fitted to one another like that of a ball-socket connection, but not limited thereto. Furthermore, tabs 1153, 1154 of coupling portion 1150 may be fitted within slots 1213, 1214 of coupling portion 1210, and wire openings 1160 of actuator 110 may be aligned with wire openings 1215a of handle 120. Given that first actuator 110 is pivotably coupled to handle 120, it is noted that tabs 1153, 1154 may be movable within slots 1213, 1214. Said coupling of tabs 1153, 1154 within slots 1213, 1214 may position and secure actuator 110 to articulate or pivot only along a single plane/trajectory/axis extending through and bisecting slots 1213 and 1214. It is noted that this plane may be the same plane within which intermediary shaft 140 may articulate or pivot relative to handle 120, as discussed in further detail below. Articulation or pivoting of actuator 110 may be performed by a finger of a hand, e.g., the thumb pushing or pulling ring 113. Moreover, the engagement of tabs of 1153, 1154 with slots 1213, 1214 may allow for the simultaneous rotation of handle 120 and secondary actuator 130 (and also intermediary shaft 140, main shaft 150, and end effector 180 as discussed below) when actuator 110 is rotated by an operator of device 100.

Figure 9D:
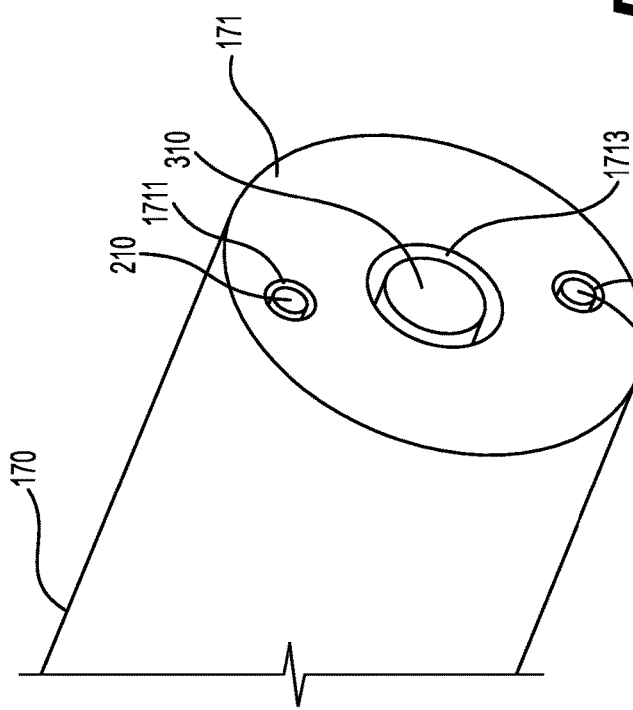
Figure 9E:
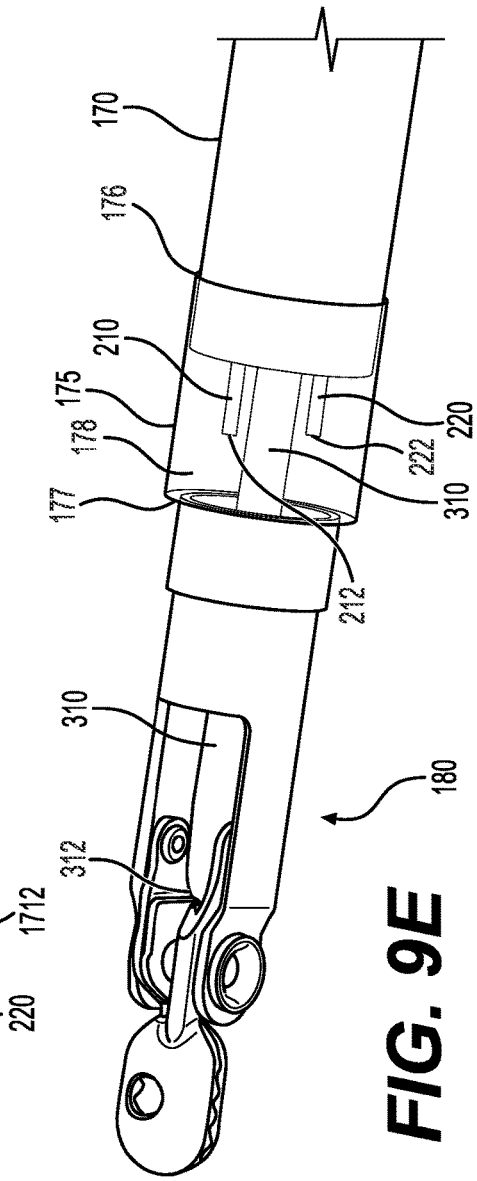

Steering wires 210 and 220 are not particularly limited, and may be any suitable wires. Steering wires 210, 220 may each include a proximal end, as shown in FIGS. 3C and 4B, and a distal end (as shown in FIG. 9E). As shown in FIGS. 3C and 4B, said proximal ends of wires 210, 220 may each be crimped via a sleeve 211, 221, e.g., an aluminum sleeve, and housed within channels of body 112. Moreover, sleeves 211, 221 may be immovably fixed within said channels of body 112. Proximal portions of wires 210 and 220 may extend distally from sleeves 211, 221, through said channels, through wire openings 160 of actutator 110, and through openings 1215a of proximal end 121 of handle 120. Thus, as actuator 110 articulates or pivots in one direction relative to handle 120, steering wire 210 or 220 may be pulled proximally, which in turn may articulate a portion of shaft 150 as discussed further below.

Second Actuator

Figure 5A:
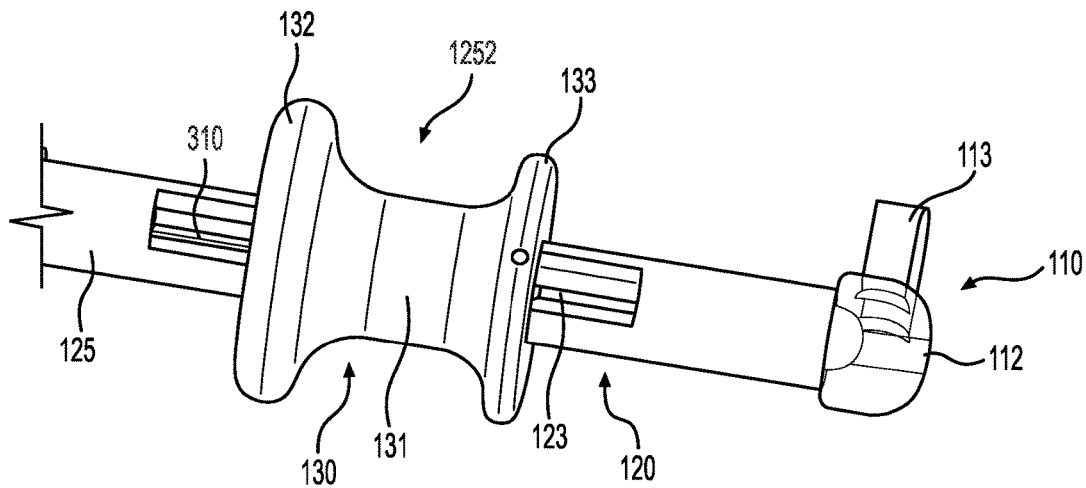
FIGS. 5A-5B are perspective views of another actuating feature of the medical device of FIGS. 2A-2F.
Figure 5B:
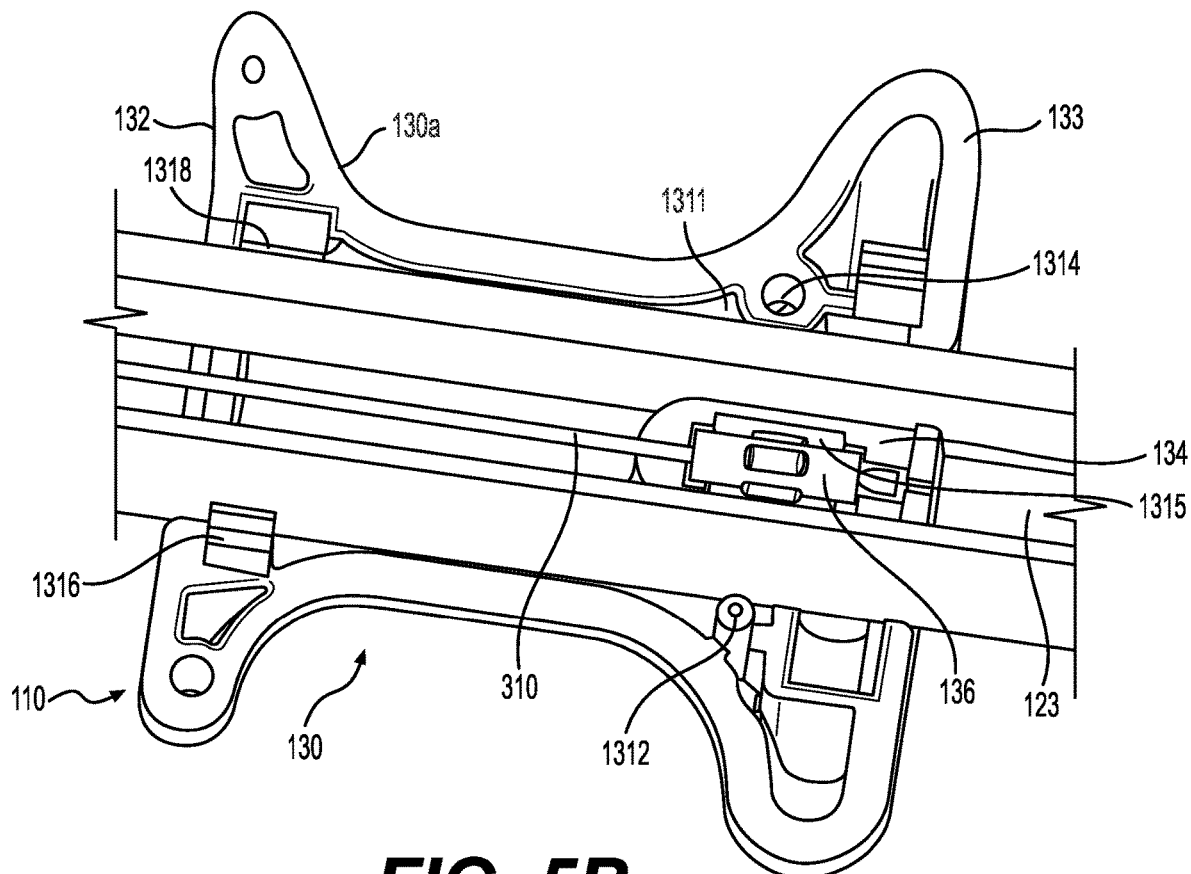

Referring to FIG. 5A, a second actuator 130 is shown. Second actuator 130 is a spool-like actuator that surrounds/sheaths a portion of body 125, and is configured to slidably translate along body 125, via recess 123 of handle 120. Actuator 130 includes a distal end 132, a middle portion 131, and a proximal end 133. Distal end 132 and proximal end 133 may protrude radially outwards relative to middle portion 131, thereby defining a recessed groove within which at least one finger or at least two fingers, e.g., an index finger and a middle finger, may rest. Moreover, protruding ends 132 and 133 may provide a surface against which said at least one finger may press against, to translate actuator 130 in a proximal/distal direction.

It is further noted that actuator 130 may be an assembled structure including two halves. For example, actuator 130 may include a first half 130a as shown in FIG. 5B, and first half 130a may include a plurality of coupling means 1312, 1314, 1316, 1318 configured to mate with corresponding coupling means present on the other half of actuator 130. Alternatively, device 100 may be assembled so that actuator 130 is a single unitary spool-like structure surrounding body 125.

FIG. 5B illustrates the coupling between first half 130a and handle 120, and pull wire 310. As shown, first half 130a further includes a first cavity 1311 and coupling portion 134, which includes a second cavity 1315. First cavity 1311 receives the portion of body 125 defining recess 123, so that actuator 130 (when assembled by coupling the two halves) encompasses said portion of body 125. While cavity 1311 receives a portion of body 125, coupling portion 134 is fitted within recess 123. Coupling portion 134 is fitted so that portion 134 may translate within the slot/channel defined by recess 123. The manner by which this is done is not particularly limited. For example, portion 134 may be shaped and sized so as to allow said portion 134 of second actuator 130 to slidably translate within recess 123, while also frictionally engaging the surfaces of body 125 around recess 123. As a result, second actuator 130 may maintain a position along body 125 in the absence of a force applied on second actuator 130. Other means, such as a track, rail, etc. may be implemented to assist with the slidable translation of actuator 130 relative to body 125.

Cavity 1315, within coupling portion 134, is configured to receive a proximal portion of pull wire 310. Moreover, said proximal portion of wire 310 may be crimped to a sleeve 136, which may be immovably fixed or locked within cavity 1315. Therefore, the translation of actuator 130 in proximal direction may translate wire 310, which in turn may actuate end effector 180. The distal translation of actuator 130, which would translate wire 310 distally, may also actuate end effector 180. For example, translating wire 310 proximally and distally, via actuator 130, may actuate the opening and closing of a grasping end effector, e.g., forceps. It is noted that the length of recess 123 defines a stroke/translation length for the actuation of end effector 180.

Intermediary Shaft

Figure 6:
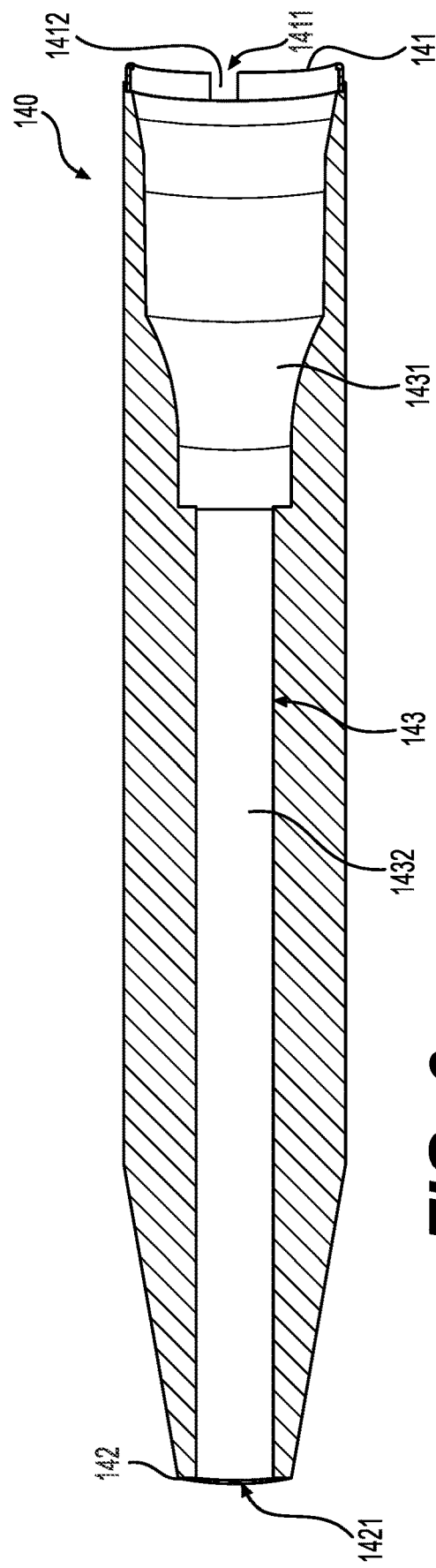
FIG. 6 is a perspective view of a shaft portion of the medical device of FIGS. 2A-2F.

Referring to FIG. 6A, an intermediary shaft 140 is shown. Shaft 140 includes a proximal end 141, a distal end 142, and a lumen 143. Proximal end 141 includes a proximal opening 1411 and two slots 1412 (only one of which is shown in FIG. 6A). Proximal opening 1411 is not particularly limited, and may be an opening configured to receive protrusion 1221 of distal coupling portion 1220. Slots 1412 are formed along a proximal edge of shaft 140. Slots 1412 are diametrically across from one another (shown in FIG. 7), and are configured to receive tabs 1222 of handle 120. Thus, proximal end 141 of shaft 140 is configured to engage and couple with distal end 122 of handle 120. Distal end 142 includes a distal opening 1421, through which main shaft 150 may extend distally.

Lumen 143 extends throughout a length of shaft 140, from proximal opening 1411 to distal opening 1421. Lumen 143 comprises two sections, a proximal cavity 1431 and channel 1432. Proximal cavity 1431 is configured to receive and house protrusion 1221 of distal end 121. Furthermore, cavity 1431 may also serve as transitional space for steering wires 210, 220, 240, 250 to flex towards channel 1432, as they extend distally through wire openings 1215d and 1240b of distal end 122 and to their respective openings on a proximal end of main shaft 50. Thus, cavity 1431 may be shaped and sized accordingly. The diameter of cavity 1431 gradually decreases as it transitions into channel 1432. Channel 1432 is configured to receive and sheath a proximal portion of main shaft 150. Channel 1432 may be of a shape and diameter configured to frictionally engage the outer surface of shaft 150, and inhibit, but not prevent, movement of main shaft 150 relative to intermediary shaft 140.

Referring to FIGS. 7A and 7B, a portion of device 100 including intermediary shaft 140 coupled to distal end 122 of handle 120, steering wires 210, 220, 240, 250, and pull wire 310 is shown. Intermediary shaft 140 is pivotably coupled to distal end 122 of handle 120 (as shown in FIG. 7A). This is done by proximal end 141 of shaft 140 engaging distal coupling portion 1220 of handle 120. More specifically, proximal opening 1411 and cavity 1431 of shaft 140 may receive partial ball/sphere-like protrusion 1221 of coupling portion 1220. For example, cavity 1431 and protrusions 1221 may be snap-fitted to one another like that of a ball-socket connection, but not limited thereto. Furthermore, tabs 1222 of coupling portion 1220 may be fitted, e.g., frictionally, within slots 1412 of shaft 140. Given that intermediary shaft 140 is pivotably coupled to distal end 122 of handle 120 (as shown in FIG. 7A), it is noted that tabs 1222 may be movable within slots 1412. Said coupling of tabs 1222 within slots 1412 may position and secure shaft 140 to articulate or pivot within a single plane/trajectory/axis defined by slots 1412. It is noted that this plane may be the same plane within which first actuator 110 may articulate or pivot relative to handle 120, as discussed previously. Articulation or pivoting of shaft 140 may be performed by a flexion of the wrist of the hand grasping device 100. Thus, an operator may actuate the primary articulation mechanism (pivoting first actuator 110 via a finger), as well as the second articulation mechanism (pivoting shaft 140 via wrist flexion), with a single hand.

It is further noted that such locking may allow for the simultaneous rotation of intermediary shaft 140 (and shaft 150) along with handle 120. Thus, the locking between actuator 110 and handle 120, the locking between intermediary shaft 140 and handle 120, and the coupling, e.g., frictional, heat shrink, etc., between main shaft 150 and intermediary shaft 140 may ensure that portions of device 100 rotate in unison when any of the aforementioned portions of device 100 is rotated, as shown in FIG. 2B.

As shown in FIG. 7B, primary steering wires 210, 220 may extend distally through distal portion 1253 of body 125 and through openings 1215d (shown in FIG. 3H) on distal end 122. Primary steering wires 210, 220 may continue to extend distally throughout cavity 1431 of shaft 140, and flex at an angle as cavity 1431 decreases in diameter and transitions into channel 1432. Wires 210, 220 may flex into their respective openings 1511, 1512 on a proximal end of main shaft 150 (shown in FIG. 9A). Proximal portions of secondary steering wires 240, 250 may be crimped, via sleeves 241, 251, to counterbores 1242 located at distal portions of channel 1241. Such crimping may fix said proximal portions of wires 240, 250 within channels 1241 of handle 120. Similar to wires 210, 220, secondary steering wires 240, 250 may extend distally through body 125 and through openings 1240b on distal end 122. Secondary steering wires 240, 250 may continue to extend distally throughout cavity 1431 of shaft 140, and flex at an angle as cavity 1431 transitions into channel 1432. Wires 240, 250 may flex into their respective openings 1513, 1514 on a proximal end of main shaft 150 (shown in FIG. 9A).

Main Shaft

Referring to FIG. 8, a main shaft 150 is shown. Shaft 150 includes a non-articulating portion 151, secondary articulation portion 160, a secondary articulation ring 165, a primary articulation portion 170, a primary articulation ring 175, and end effector 180. Portion 151 is not particularly limited, and may be, as discussed above, any suitable multi-lumen shaft.

Non-articulating portion 151 extends distally between a proximal end of main shaft 150 to secondary articulation portion 160. Thus, a proximal end 152 of non-articulating portion 151, shown in FIG. 9A, is fixed within channel 1432, e.g., via frictional fit, heat shrink, etc., as shown in FIG. 7B. A proximal end 152 of portion 151 includes steering wire openings 1511, 1512, 1513, 1514, and a pull wire opening 1515. Opening 1515 is configured to receive pull wire 310 and accommodate for the proximal/distal translation of wire 310 through opening 1515. Opening 1515 is centrally located on a proximal surface of proximal end 152.

Primary steering wire openings 1511, 1512 are respectively configured to receive primary steering wires, 210, 220, and second steering wire openings 1513, 1514 are respectively configured to receive second steering wires, 240, 250. Openings 1511, 1512, 1513, 1514 lie on the proximal surface of proximal end 152, surrounding central opening 1515. It is noted that openings 1511 and 1512 are positioned diametrically across from each another, and likewise, openings 1513 and 1514 are positioned diametrically across from each other. Thus, openings 1511, 1512, 1513, 1514, while surrounding opening 1515, may be arranged so that each of the distances between an opening 1215d and an opening 1240b are the equal. The arrangement of the aforementioned openings on proximal end 152 may mirror the arrangement of openings on distal end 122 of handle 120, to ease the transition of wires 210, 220, 240, 250, and 310 into shaft 150.

FIG. 9B illustrates a cross-section of secondary articulation portion 160. As can be seen, the arrangement of wires 210, 220, 240, 250, and 310 is consistent with that of non-articulating portion 151, as shown in FIG. 9A.

As shown in FIG. 9C, secondary articulation portion 160 transitions into secondary articulation ring 165. Ring 165 includes a proximal opening 166, a distal opening 167, and a cavity 168 in between. Proximal opening 166 (and cavity 168) is configured to receive a distal end/portion of secondary articulating portion 160, including wires 210, 220, 240, 250, and 310. The manner by which proximal opening 166 of ring 165 couples to the distal end/portion of articulating portion 160 is not particularly limited, and may be, for example, via a frictional fit. Cavity 168 of ring 165 is configured to receive and house wires 210, 220, 240, 250, and 310. Distal opening 167 of ring 165 is configured to receive a proximal end 171 of articulating portion 170 via any suitable means, e.g., a frictional fit.

Pull wire 310 extends distally via a straight, linear manner into an opening 1713 (shown in FIG. 9D) on a proximal end 171 of primary articulating portion 170. Secondary steering wires 240, 250 may extend distally within cavity 168 of ring 165, up until a point between the distal end of portion 160 and a proximal end 171 of portion 170, e.g., a midpoint or other point of said cavity 168. The distal ends 242, 252 of wires 240, 250 may be affixed or welded within ring 165, thereby providing leverage for secondary steering wires 240, 250 to articulate both ring 165 and secondary articulating portion 160 as wire 240 or 250 is pulled proximally. For example, distal ends 242, 252 may be welded to an inner surface of ring 165 or a partially solid portion of cavity 168. As discussed above, such articulation, e.g., the secondary articulation mechanism, may be actuated via the pivoting of handle 120 relative to intermediary shaft 140 (or vice versa).

Primary steering wires 210, 220 may extend distally throughout cavity 168 of ring 165 towards primary articulating portion 170. As shown in FIG. 9C, wires 210, 220 respectively have a curved portion 215, 225 that curves at an angle while extending towards a proximal end 171 of primary articulating portion 170. Wires 210, 220 extend, via portions 215, 225, toward wire openings 1711, 1712 (shown in FIG. 9D) of proximal end 171, which are oriented 90°, or approximately 90°, about a longitudinal axis of shaft 150, relative to the orientation of openings 1511, 1512. Therefore, primary steering wires 210, 220 re-orient, while extending into primary articulating portion 170, so that wires 210, 220, 240, and 250 extend along a shared plane, as shown in FIG. 9C. Wires 210, 220, 240, and 250 may extend along a shared plane throughout a length of the portion of wires 210, 220 distal to curved portions 215, 225, e.g., greater than 1 cm, 2 cm, 3 cm, 4 cm, 5 cm, etc. Furthermore, it is noted that the portions of wires 210, 220 proximal to curved portions 215, 225 and the portions of wires distal to curved portions 215 travel in offset but parallel lumens.

FIG. 9D illustrates a section view of proximal end 171 of primary articulation portion 170. As can be seen, proximal end 171 includes steering wire openings 1711, 1712, and a pull wire opening 1713. As noted above, opening 1713 is configured to receive pull wire 310 and accommodate for the proximal/distal translation of wire 310 through opening 1713. Opening 1713 is centrally located on a proximal surface of proximal end 152. Thus, opening 1713 maintains alignment with opening 1515 (shown in FIG. 9A) of non-articulating portion 151. Primary steering wire openings 1711, 1712 are respectively configured to receive primary steering wires, 210, 220. Openings 1711, 1712, lie on a proximal surface of proximal end 171, around central opening 1713. It is noted that openings 1711 and 1712 are positioned diametrically across from each another. Furthermore, as previously noted, openings 1711 and 1712 guide wires 210, 220 along the same plane as secondary steering wires 240, 250.

As shown in FIG. 9E, primary articulation portion 170 transitions into primary articulation ring 175. Ring 175 includes a proximal opening 176, a distal opening 177, and a cavity 178 in between. Proximal opening 176 (and cavity 178) is configured to receive a distal end/portion of primary articulating portion 170, including wires 210, 220, and 310. The manner by which proximal opening 176 of ring 175 couples to the distal end/portion of articulating portion 170 is not particularly limited, and may be, for example, via a frictional fit. Cavity 178 of ring 175 is configured to receive and house wires 210, 220, and 310. Distal opening 177 of ring 175 is configured to receive a proximal end/portion of end effector 180 via any suitable means, e.g., a frictional fit.

Pull wire 310 extends distally via a straight, linear manner towards end effector 180. Primary steering wires 210, 220 may extend distally within cavity 178 of ring 175, up until a point between the distal end of articulating portion 170 and a proximal end of end effector 180, e.g., a midpoint of said cavity. The distal ends 212, 222 of wires 210, 220 may be affixed or welded within ring 175, thereby providing leverage for primary steering wires 210, 220 to articulate both ring 175 and primary articulating portion 170 as wire 210 or 220 is pulled proximally. For example, distal ends 212, 222 may be welded to an inner surface of ring 175 or a partially solid portion of cavity 178. As discussed above, such articulation, e.g., the primary articulation mechanism, may be actuated via the pivoting of first actuator 110 relative to handle 120 (or vice versa).

Thus, in view of the above, it is noted that the pivoting of first actuator 110 relative to handle 120, the pivoting of handle 120 relative to intermediary shaft 140, the articulation of secondary articulation portion 160, and the direction of primary articulation portion 170 all are restricted to the same plane. This is shown in FIGS. 2C-2F. As shown in FIG. 2C, pivoting first action 110 in a distal direction (indicated by directional arrow A) articulates primary articulating portion 170 in a downward direction, in which the pivoting direction and the articulation direction are along the same plane. Likewise, as shown in FIG. 2D, pivoting handle 120 in a downward direction (indicated by directional arrow B) articulates secondary articulating portion 160 in a downward direction, in which the pivoting direction and the articulation direction, again, are along the same plane. The same is shown in FIGS. 2E and 2F when pivoting actuator 110 and handle 120 in the opposite direction. As shown in FIG. 2E, pivoting first action 110 in a proximal direction (indicated by directional arrow C) articulates primary articulating portion 170 in an upward direction, in which the pivoting direction and the articulation direction are along the same plane. Likewise, as shown in FIG. 2F, pivoting handle 120 in a upward direction (indicated by directional arrow D) articulates secondary articulating portion 160 in an upward direction, in which the pivoting direction and the articulation direction, again, are along the same plane.

End Effector

End effector 180 is not particularly limited. For example, end effector 180 may be any one of a cautery knife, biopsy forceps, tissue grasper jaws, cautery snare, hemostatis clip, suturing wire, or any other suitable end effector. End effector 180 may include a proximal end that may be removably coupled to the distal opening of primary articulation ring 175. For example, end effector 180 may be frictionally fitted to said distal opening, so that it end effector 180 may be removed and substituted with other end effectors that may be preferred. End effector 180 may also be coupled to a distal end 312 of pull wire 310. Wire 310 may couple to end effector 180 via any suitable manner, so that the translation of wire 310 in either a proximal or distal direction triggers an actuation of end effector 180, e.g., opening/closing of foreceps.

Method of Use

Referring to FIGS. 1A-2A, an example of how medical system 10 and device 100 may be used is further discussed below. A user may deliver a distal end of tube 56 of scope 50 into the body of a subject, e.g., via a natural orifice (such as a mouth or anus) and through a tortuous natural body lumen of the subject, such as an esophagus, stomach, colon, etc., towards a targeted site. The user may couple device 70, via first end 71, to port 54, before or after tube 56 is delivered to the targeted site. While grasping device 100 via a single hand (or two hands in other examples), the distal end of device 100 may be inserted into a second end 73 of device 70, and guided through port 54, and delivered to the targeted site, for example, through a working channel of scope 50. Once delivered, the user may further adjust the position of end effector 180 relative to the targeted site by any one of the following manners: 1) a user may rotate end effector 180 by rotating first actuator 110, via the single hand, in a clockwise or counter-clockwise direction; 2) a user may proximally/distally translate end effector 180 by a translation of the single hand while holding device 100; 3) a user may articulate end effector 180 in one direction by pivoting first actuator 110 relative to handle 120 using the thumb of the single hand; and 4) a user may further articulate end effector 180 in the same direction by pivoting handle 120 relative to intermediary shaft 140 by flexion of the wrist of the single hand. After adjusting the position of end effector 180, the user may actuate end effector 180 by slidably translating second actuator 130 relative to handle 120 via at least one finger, e.g., index and middle fingers, of the single hand.

Single Articulation Devices

While medical device 100, as described above, offers articulation at two different sections of shaft 150, e.g., articulation portions 160, 170, via two different joints, e.g., first actuator 110-handle 120 and handle 120-intermediary shaft 140, other exemplary embodiments may be single articulation devices.

Figure 10:
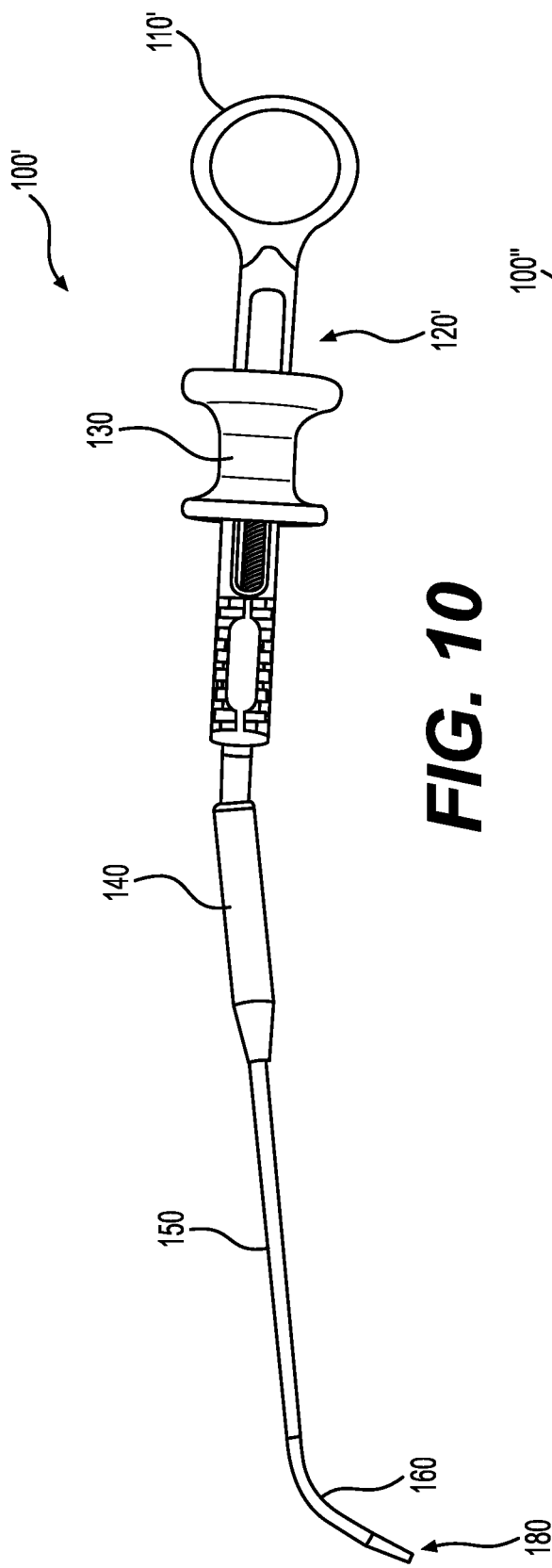
FIG. 10 is a perspective view of another medical device, according to other aspects of the present disclosure.

FIG. 10 illustrates an exemplary single articulation device 100'. Device 100' is similar to device 100 in some respects, and like reference numerals refer to like parts. Unlike device 100, device 100' is without a pivotable first actuator 110, and includes a ring 110', which may be unitary with a proximal end of handle 120'. Thus, device 100' may only include a single joint between intermediary shaft 140 and a distal end of handle 120'. Furthermore, device 100' may include a single articulation portion 160 along shaft 150. The manner by which portion 160 may be articulated via the pivoting between shaft 140 and handle 120' may be the same as (or similar to) device 100.

Figure 11:
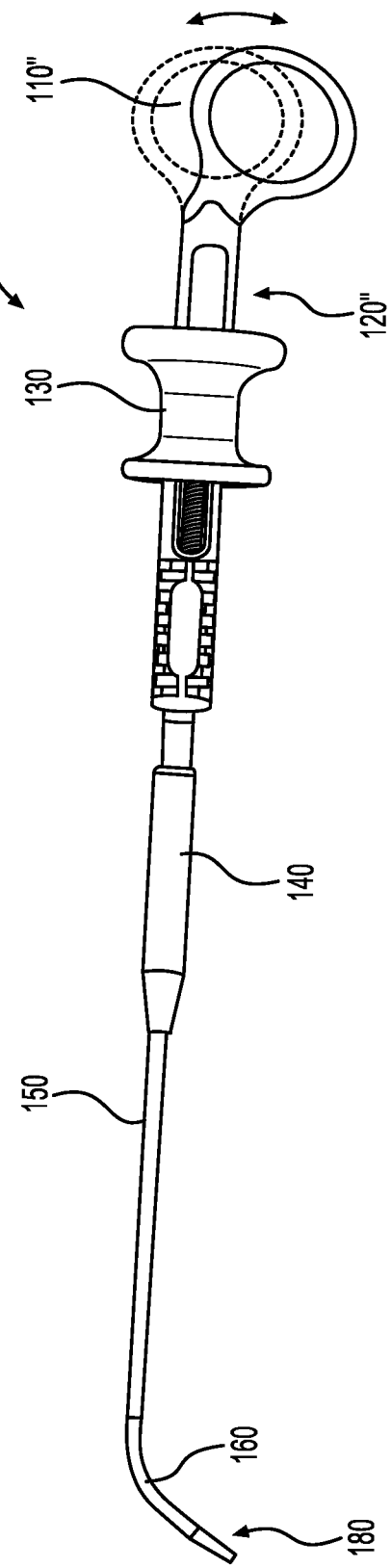
FIG. 11 is a perspective view of another medical device, according to some other aspects of the present disclosure.

FIG. 11 illustrates an exemplary single articulation device 100". Device 100" is similar to device 100 in some respects, and like reference numerals refer to like parts. Unlike device 100, device 100" is without a pivotable connection between intermediary shaft 140" and handle 120". Thus, device 100" may only include a single joint between first actuator 110" and a proximal end of handle 120". As shown, actuator 110" may be without a ball/sphere shaped body, like actuator 110 of device 100, and may simply be a ring that is pivotably coupled to a proximal end of handle 120". Device 100" may also include a single articulation portion 160 along shaft 150. The manner by which portion 160 may be articulated via the pivoting between actuator 110" and handle 120" may be the same as (or similar to) device 100.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
a handle extending between a first end and a second end;
a first actuator coupled to the first end of the handle;
a first shaft coupled to the second end of the handle; and
a second shaft extending from the first shaft, the second shaft including a first articulation section and a second articulation section,
wherein an articulation of the first actuator relative to the handle is configured to articulate the first articulation section, an articulation of the handle relative to the first shaft is configured to articulate the second articulation section, and the first articulation section and the second articulation section are restricted to articulating only in a first plane.

2. The medical device of claim 1, wherein the first actuator is configured to articulate relative to the handle within only the first plane and the handle is configured to articulate relative to the first shaft within only the first plane.

3. The medical device of claim 1, wherein the handle, the first actuator, the first shaft, and the second shaft are configured so that they must rotate together about a longitudinal axis of the medical device in unison.

4. The medical device of claim 1, wherein the first actuator is pivotably coupled to the first end of the handle so that the first actuator is configured to pivot relative to the handle within only the first plane.

5. The medical device of claim 1, wherein the second end of the handle is pivotably coupled to the first shaft so that the handle is configured to pivot relative to the first shaft within only the first plane.

6. The medical device of claim 1, wherein the second articulation section is proximal to the first articulation section.

7. The medical device of claim 1, wherein the second shaft further includes a non-articulating section adjacent to the second articulation section, a first articulation coupler coupled to a first end of the first articulation section, and a second articulation coupler coupling a second end of the first articulation section to a first end of the second articulation section.

8. The medical device of claim 7, further comprising a first wire, a second wire, a third wire, and a fourth wire, wherein each of the first wire and the second wire includes a first end fixed within the first actuator, and each of the third wire and the fourth wire includes a first end fixed within a portion of the handle, and wherein the first wire and the second wire are configured to articulate the first articulation section, and the third wire and the fourth wire are configured to articulate the second articulation section.

9. The medical device of claim 8, wherein each of the first wire and the second wire further includes a second end fixed within the first articulation coupler, and each of the third wire and the fourth wire further includes a second end fixed within the second articulation coupler.

10. The medical device of claim 9, wherein longitudinally-extending portions of the second ends of the first wire, the second wire, the third wire, and the fourth wire extend along a shared plane.

11. The medical device of claim 1, further comprising an end effector and a second actuator configured to actuate the end effector, wherein the second actuator is coupled to a portion of the handle between the first end and the second end, and the second actuator is slideably coupled to the handle so that the second actuator may translate along the portion of the handle between the first end and the second end.

12. The medical device of claim 11, wherein the first shaft is coupled to the second end of the handle via a ball and socket connection.

13. The medical device of claim 12, wherein the first actuator is coupled to the first end of the handle via a ball and socket connection.

14. The medical device of claim 1, further comprising a second actuator, wherein the first actuator and the second actuator are positioned relative to each other so that the first actuator is accessible by a first finger of a hand and the second actuator is accessible by a second finger of the hand without changing a position of the hand relative to the medical device.

15. The medical device of claim 14, wherein the handle is configured to be articulated via a flexion of the hand.

16. A medical device comprising:
a handle extending between a first end and a second end;
a first actuator pivotably coupled to the first end of the handle;
a first shaft pivotably coupled to the second end of the handle;
a second shaft extending from the first shaft, the second shaft including a first articulation section and a second articulation section;
a first set of connectors between the first actuator and the first end of the handle, wherein said first set restricts a pivoting of the first actuator to a first pivot axis; and
a second set of connectors between the first shaft and the second end of the handle, wherein said second set restricts a pivoting of the first shaft to a second pivot axis,
wherein the pivoting of the first actuator relative to the handle is configured to articulate the first articulation section and the pivoting of the handle relative to the first shaft is configured to articulate the second articulation section.

17. The medical device of claim 16, wherein the first pivot axis and the second pivot axis are co-planar.

18. The medical device of claim 17, wherein the first set of connectors includes slots and tabs received by the slots.

19. The medical device of claim 18, wherein the second set of connectors includes slots and tabs received by the slots.

20. A method of positioning a shaft of a medical device, comprising:
inserting a distal end of the shaft of the medical device into a body of a subject;
articulating a first actuator of the medical device relative to a handle of the medical device to articulate the shaft in a first direction, wherein said articulation is restricted by configuration of the medical device to a single plane; and
articulating the handle relative to an intermediary shaft of the medical device to articulate the shaft in a second direction, wherein said articulation is restricted by the medical device to the single plane.

* * * * *